United States Patent
McHugh et al.

(10) Patent No.: US 12,318,300 B1
(45) Date of Patent: Jun. 3, 2025

(54) TIBIAL INSERT WITH VARIABLE ARTICULAR SURFACE

(71) Applicant: Joint Development, Inc., Salt Lake City, UT (US)

(72) Inventors: Dermott J. McHugh, Salt Lake City, UT (US); Eric M. Dacus, Salt Lake City, UT (US); Chris A. Weaber, Sandy, UT (US)

(73) Assignee: Joint Development, Inc., Salt Lake City, UT (US)

( * ) Notice: Subject to any disclaimer, the term of this patent is extended or adjusted under 35 U.S.C. 154(b) by 0 days.

(21) Appl. No.: 18/763,882

(22) Filed: Jul. 3, 2024

(51) Int. Cl.
*A61F 2/38* (2006.01)
*A61F 2/30* (2006.01)

(52) U.S. Cl.
CPC .......... *A61F 2/389* (2013.01); *A61F 2/30734* (2013.01); *A61F 2002/30131* (2013.01); *A61F 2002/30449* (2013.01); *A61F 2002/3895* (2013.01)

(58) Field of Classification Search
CPC .... A61F 2/389; A61F 2/3868; A61F 2/30734; A61F 2002/3895; A61F 2002/30131; A61F 2002/30449
See application file for complete search history.

(56) References Cited

U.S. PATENT DOCUMENTS

2003/0100953 A1* 5/2003 Rosa .................. A61F 2/38
623/20.32

* cited by examiner

*Primary Examiner* — Dinah Baria
(74) *Attorney, Agent, or Firm* — Lowry Blixseth APC; Scott M. Lowry

(57) ABSTRACT

The tibial insert includes a base having a coupling for attachment to a tibial baseplate, and an upwardly presented articular surface formed from the base, which includes a concave troughed geometry having a progressively larger medial-to-lateral frontal cross-section opening anteriorly to posteriorly along a length of the tibial insert.

24 Claims, 19 Drawing Sheets

TIBIAL INSERT WITH VARIABLE ARTICULAR SURFACE

BACKGROUND OF THE INVENTION

The present invention generally relates to a tibial insert. More specifically, the present invention is directed to a tibial insert having a variable articular surface geometry that includes a concave opening progressively enlarging in a medial-to-lateral frontal cross-section anteriorly to posteriorly to decrease congruence with an articulating surface of a femoral component during movement from extension to flexion.

Knee replacement surgery, also known as knee arthroplasty, is a surgical procedure that involves removing and/or replacing worn-out or damaged parts of a knee joint with an artificial joint called an orthopedic prosthesis. This procedure is typically carried out when the knee joint becomes severely damaged by conditions such as osteoarthritis or rheumatoid arthritis. As such, surgery may involve removing and/or replacing parts of the knee or the entire end of the femur and/or tibia, depending on the severity of the damage. The implanted orthopedic components that replace the damaged parts of the knee joint are designed to mimic the function and operation of a normal knee, and may be made of metal alloys, high-grade plastics, or ceramic materials. Once the surgery is complete, the implanted orthopedic prosthesis is designed to improve knee function, enhance mobility, and reduce pain.

More specifically, the type of knee replacement surgery depends on the extent of the damage to the knee and the parts thereof that require replacement. In one procedure, total knee replacement ("TKR") surgery involves removing the entirety of the ends of the femur and tibia, and then reshaping each to receive the artificial orthopedic components. TKR involves replacing the entire knee joint with the joint prosthesis as a result. In less severe conditions, other surgical procedures such as unicompartmental (partial) knee replacement and minimally invasive knee replacement involve removing less than the entire knee. Unicompartmental knee replacement surgery, e.g., has been in use for more than 50 years and involves removing and replacing damaged portions of the knee with the orthopedic implants, while retaining or preserving healthy portions thereof. As a result, unicompartmental knee replacement surgery usually involves incisions that are relatively smaller than those required to perform total knee replacement surgery and patients usually spend little or no time in the hospital after the surgery is complete. As such, patients who undergo unicompartmental knee replacement surgery can usually return to normal activities sooner than TKR patients.

More specifically, unicompartmental knee replacement surgery usually involves removing and replacing one of the femoral condyles (instead of both condyles as in TKR) at the lower end of the femur with an artificial femoral component designed to serve as a new articulatory surface relative to the tibia. As such, the curvature of the artificial femoral component is designed to replicate the contours of the natural femur condyle to mimic natural knee kinematics during use after the surgery is complete. Additionally, in unicompartmental knee replacement surgery, a portion of the tibia underneath the implanted artificial femoral component may be removed and replaced with an artificial tibial component having an upper surface that interfaces with the artificial femoral component in articulatory relation relative thereto. The tibial component is typically made from a metal plate that attaches to the tibia, and a plastic insert made from polyethylene or the like attaches to the top of the tibial component and acts as a cushion to provide smoother articulation with the replaced femoral condyle.

In this respect, tibial inserts known in the art either have a flat surface, a nearly flat surface, or a perfectively spherical surface. While flat or nearly flat surface designs have been widely adopted in the industry, one problem is that, during flexion, the femoral component contacts the posterior side of the tibial insert articular surface at a location that creates a point load thereon. Point loads on the articular surface cause an undesirable increase in contact stresses and wear on the tibial insert articular surface over time. These relatively high stresses are known to cause increased wear and early failure of the prosthesis as a result. Moreover, posterior point contact of the femur on the tibial insert articular surface can cause a moment across the frontal plane thereof. This leads to a reciprocal upward force on the anterior side of the insert that urges an anterior lip of the insert to pull away from the tibial baseplate to which the insert is secured. With enough force, the cement bonding the tibial insert to the tibial baseplate can loosen and fail such that the tibial insert undesirably pulls away from the baseplate. This same problem can also arise in cementless designs and failure in either cemented or cementless designs requires that the patient undergo undesirable revision surgery to fix the issue.

Similarly, flat inserts can also fail in fixed bearing designs as the result of a single point of contact edge loading that causes the anterior portion of the insert to lift up off the tibial component due to improper posterior loading of the femur on the insert.

Additionally, fully spherical inserts have a uniform concave articular surface that matches a convex surface of the femoral component condyle. Tibial inserts with uniform concave articular surfaces are relatively more complex than flat or nearly flat designs and, as a result, have higher manufacturing costs. Moreover, while fully spherical mobile bearing articular surfaces have been used with good clinical success, the industry has yet to see widespread adoption outside a single implant due to difficulties meeting the Class 3 regulatory designation of the Food and Drug Administration ("FDA"). Additionally, while uniform concave articular surfaces can reduce point loads on the tibial insert, the matching concave/convex surfaces create needless constant contact across nearly the entire articular surface between extension and flexion. This, in turn, causes the femoral component to constantly rub against the concave articular surface of the tibial insert more than designs that utilize flat or nearly flat insert surfaces. This undesirably results in additional wear on the tibial insert and femoral component over time. Additionally, the fact that spherical inserts provide more constraint between the articular surface of the insert and femoral component when moving from extension to flexion is also undesirable because it is a poor replication of natural knee kinematics.

Furthermore, as the anatomy of a patient knee joint differs from person to person, femoral components, tibial baseplates, and tibia inserts may vary in size and shape. As such, manufacturing, inventory, and sterilization costs are already relatively high to accommodate the various patient knee joint anatomies and manufacturers must retain adequate inventory for right knees and left knees as prior art designs are asymmetrical. In view that the number of patients needing a joint replacement continues to increase year-over-year, knee arthroplasty procedures can become more cost effective and accessible through use of universally symmetrical components designed for implantation in the right knee or the left knee. Although, achieving equivalent clinical function without left and right components creates additional constraints and challenges.

There exists, therefore, a significant need in the art for a tibial insert that includes a variable articular surface geometry that includes a concave geometry having a progressively larger medial-to-lateral cross-section when moving anteriorly to posteriorly such that a femoral component condyle becomes progressively less congruent therewith when moving from full extension to full flexion. The present invention fulfills these needs and provides further related advantages.

SUMMARY OF THE INVENTION

One embodiment of a tibial insert as disclosed herein may include a base having a coupling on one side for attachment to a tibial baseplate and an upwardly presented variable articular surface formed from the base on an opposite side of the coupling thereof. The coupling may include a trough formed within the base having a depth to receive a quantity of bone cement sufficient to couple the base to the tibial baseplate as part of unicompartmental (partial) knee replacement. Additionally, the upwardly presented variable articular surface may include a concave geometry having a progressively larger medial-to-lateral frontal cross-section opening anteriorly to posteriorly at least partially along a length of a posterior portion of the tibial insert. In this respect, the concave geometry of the variable articular surface may be relatively more lofted at an anterior edge of the tibial insert than midway between the anterior edge and a posterior edge. Alternatively, or in addition to, the concave geometry may also be relatively more lofted at a posterior edge of the tibial insert than midway between the posterior edge and an anterior edge. The concave geometry itself may be that of a circular curve, a parabolic curve, an elliptical curve, a spline curve, or a trough.

In another aspect of these embodiments, the concave geometry may include a variable radius of curvature that progressively increases in size anteriorly to posteriorly along an entire length of the tibial insert, and the posterior portion of the tibial insert may be between a posterior edge and midway between the posterior edge and an anterior edge (i.e., the center of the tibial insert). In another aspect of these embodiments, the articular surface may be symmetrical, such as being anteriorly-to-posteriorly symmetrical and/or medially-to-laterally symmetrical, or the articular surface may be partially of entirely asymmetrical, such as being asymmetrical about one or both of the coronal and/or median planes. The tibial insert may also be manufactured as a singular component implantable with a medial condyle component or a lateral condyle component in a left knee unicompartmental knee replacement and/or a right knee unicompartmental knee replacement.

In another embodiment as disclosed herein, the tibial insert may include a base having a coupling for attachment to a tibial baseplate and an articular surface formed from the base having a pair of concave geometries tapering interiorly in height and progressively decreasing in a medial-to-lateral frontal cross-section from a respective anterior edge to a posterior edge of the tibial insert. Each of the pair of concave geometries may be symmetrical relative to one another about a coronal plane and/or about a median plane, or each of the of concave geometries may be asymmetrical relative to one another. In another aspect of these embodiments, the articular surface may at least partially taper interiorly in height between at least one of the anterior edge or the posterior edge and midway between the anterior edge and the posterior edge. Additionally, at least one of the concave geometries may be a circular curve, a parabolic curve, an elliptical curve, or a spline curve, or a trough. The tibial insert may also be made as a singular component implantable with a lateral condyle component or a medial condyle component in either a right knee unicompartmental knee replacement or a left knee unicompartmental knee replacement.

In another embodiment, the tibial insert disclosed herein may include a base having a coupling for attachment to a tibial baseplate and an articular surface formed from the base having a symmetrical medial-to-lateral frontal cross-section opening relatively larger at a posterior edge and an anterior edge of the base than at a center thereof independent of the orientation of the tibial insert in a left unicompartmental knee replacement or a right unicompartmental knee replacement. As such, the tibial insert may be manufactured as a singular component wherein the articular surface is anterior-to-posterior symmetrical and/or medial-to-lateral symmetrical such that the tibial component is implantable with a medial condyle component or a lateral condyle component in a left knee unicompartmental knee replacement or a right knee unicompartmental knee replacement.

In one embodiment, the symmetrical medial-to-lateral frontal cross-section opening may be that of a troughed geometry that tapers from the posterior edge and tapers from the anterior edge of the tibial insert to the center thereof. The articular surface may include a variable radius of curvature relatively larger than a constant radius of curvature of a translating surface of a femoral component, e.g., on the order of a ratio of 5:1 at ninety degrees flexion and a ratio of 2.5:1 at zero degrees flexion. In this respect, the translating surface of the femoral component may maintain a relatively constant contact patch with the articular surface of the tibial insert between zero degrees flexion and ninety degrees flexion, and the variable radius of curvature may permit at least ±10 degrees of internal or external rotation of the femoral component relative to the tibial insert between zero degrees flexion and ninety degrees flexion.

Additionally, the coupling may be a bone cement selected from the group consisting of a polymethylmethacrylate (PMMA) adhesive, a fibrin adhesive, a collagen adhesive, a polyurethane adhesive, an epoxy resin adhesive, a cyanoacrylate adhesive, a polyester adhesive, and a zinc polycarboxylate adhesive. Alternatively, the coupling may be a cementless attachment selected from the group consisting of a snap, a threaded screw, a bolt, a locking cross pin, and a metal clip.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
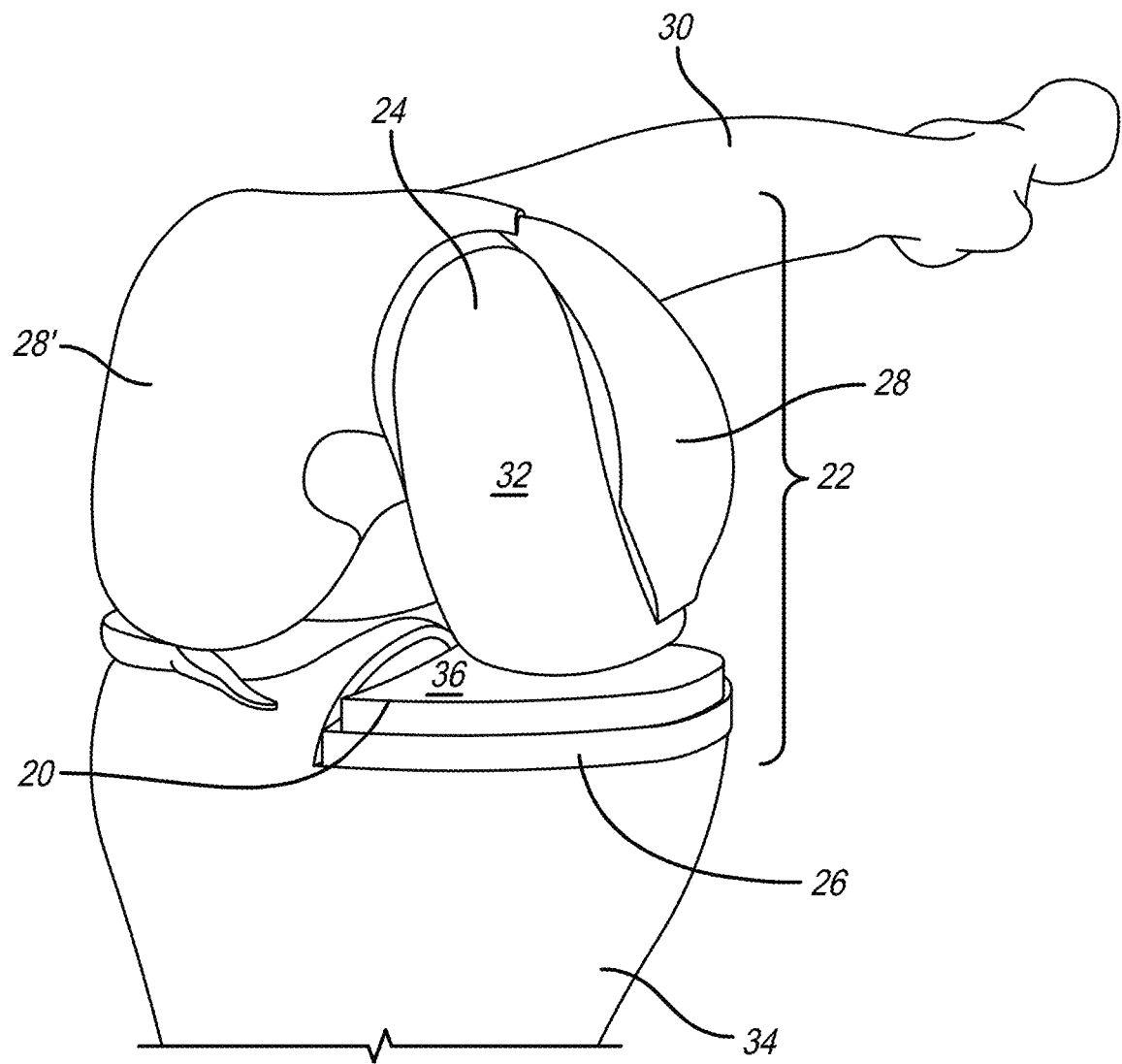
FIG. 1 is an environmental perspective view of a unicompartmental knee replacement in a flexion position.

As shown in the exemplary drawings for purposes of illustration, the present invention for a tibial insert 20 having several different types of variable articular surfaces as disclosed herein is generally illustrated in FIGS. 1-21. As briefly mentioned above, unicompartmental knee replacement surgery differs from total knee replacement surgery in that a portion of the knee (as opposed to replacing the entire knee) is surgically repaired. As such, the tibial insert 20 is one of several orthopedic implant components for use in a unicompartmental knee replacement system 22 along with a femoral component 24 and a tibial baseplate 26, such as those illustrated in FIGS. 1 and 2. In this respect, FIG. 1 more specifically illustrates one embodiment wherein a condyle 28 of a pair of condyles 28, 28' of a patient femur 30 has been resurfaced to selectively receive the femoral component 24. Here, the remainder of the patient femur 30, including the condyle 28', remain substantially unaltered. The femoral component 24 is illustrated in FIG. 1 having a curved articular surface 32 designed to mimic the natural articular surface of the natural condyle the femoral component 24 replaces. A portion of a patient tibia 34 located directly underneath the femoral component 24 of the surgically repaired condyle 28 is resurfaced to selectively receive and retain the tibial baseplate 26 therein. The tibial baseplate 26 selectively receives and retains the tibial insert 20 in a position underneath the femoral component 24 so the curved articular surface 32 thereof articulates across a variable articular surface 36, the various embodiments and features of which are disclosed in more detail herein.

Figure 2:
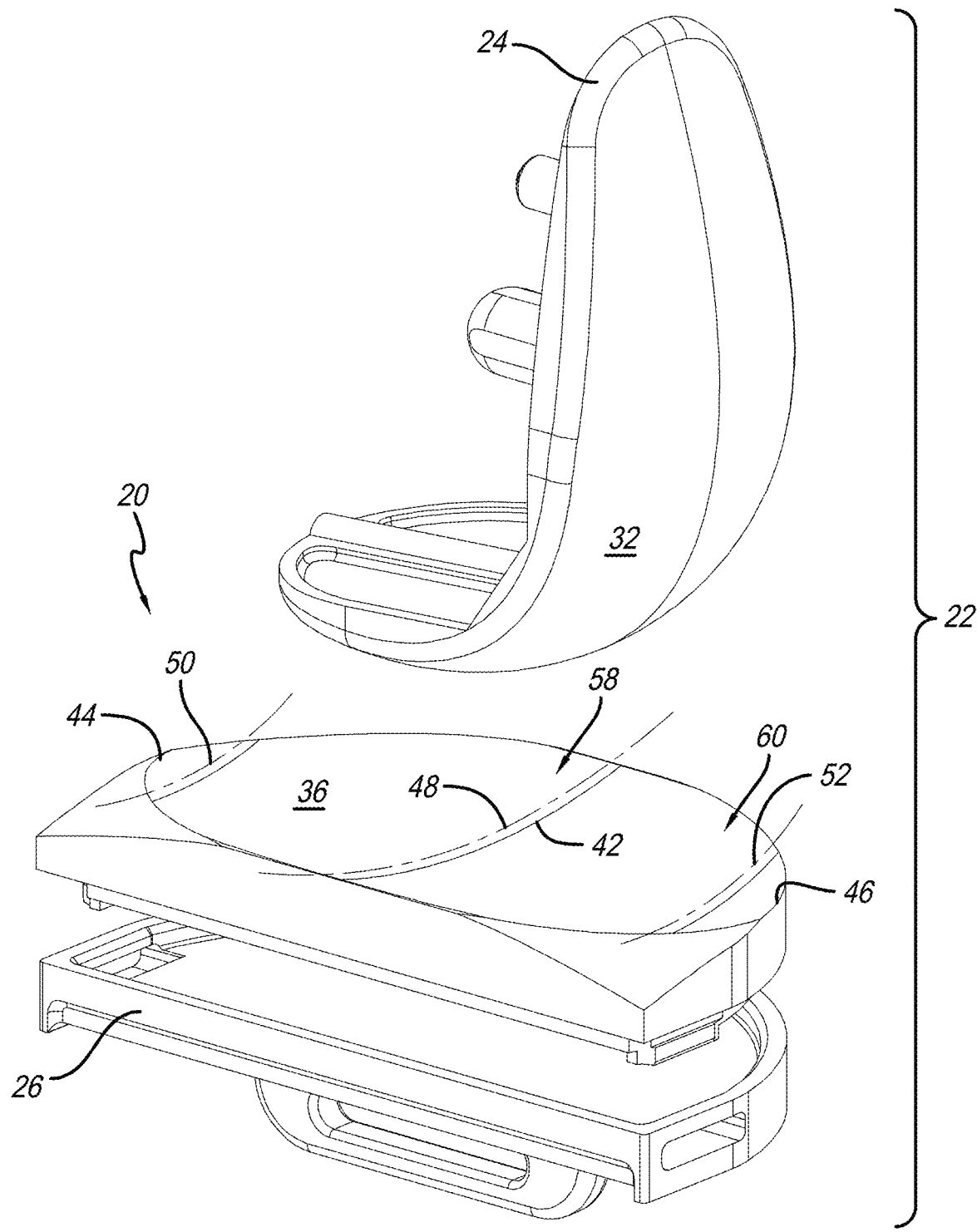
FIG. 2 is an exploded perspective view of the unicompartmental knee replacement of FIG. 1 prior to implantation, more specifically illustrating one embodiment of a tibial insert as disclosed herein having a variable articular surface generally positioned underneath a curved surface of a femoral component for articulation relative thereto.
Figure 3:
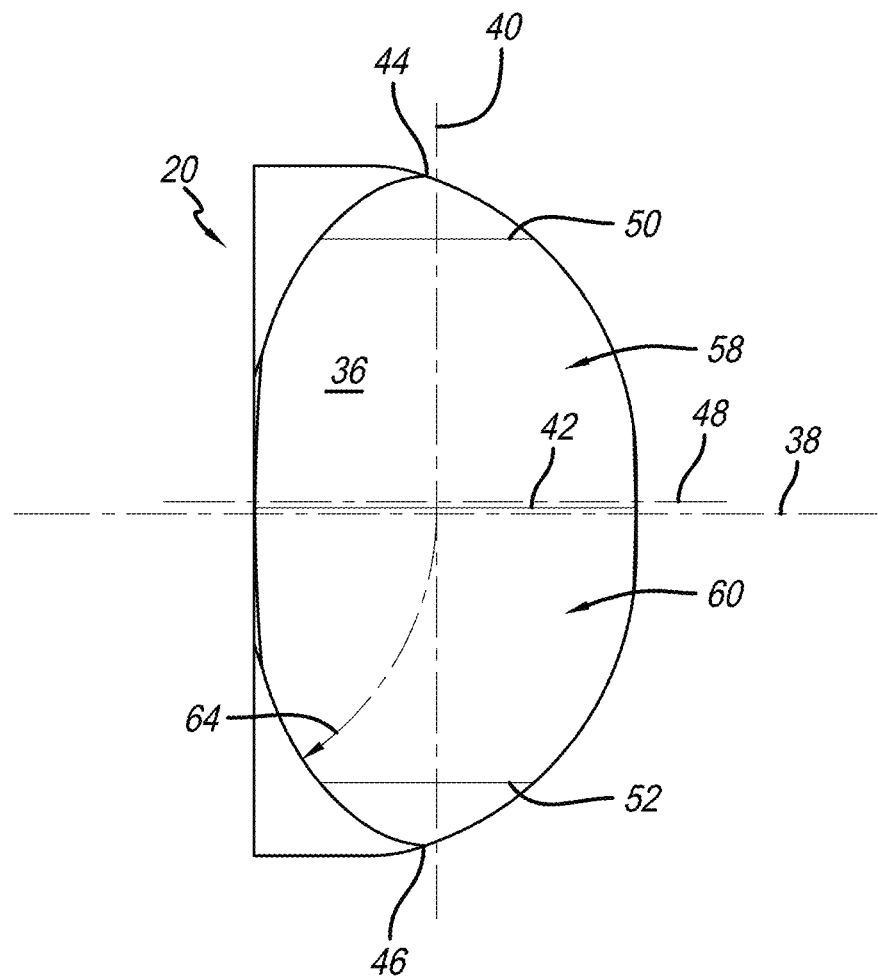
FIG. 3 is a top plan view of the tibial insert of FIG. 2, further illustrating one embodiment where the variable articular surface is symmetrical about a coronal plane and symmetrical about a median plane.
Figure 4:
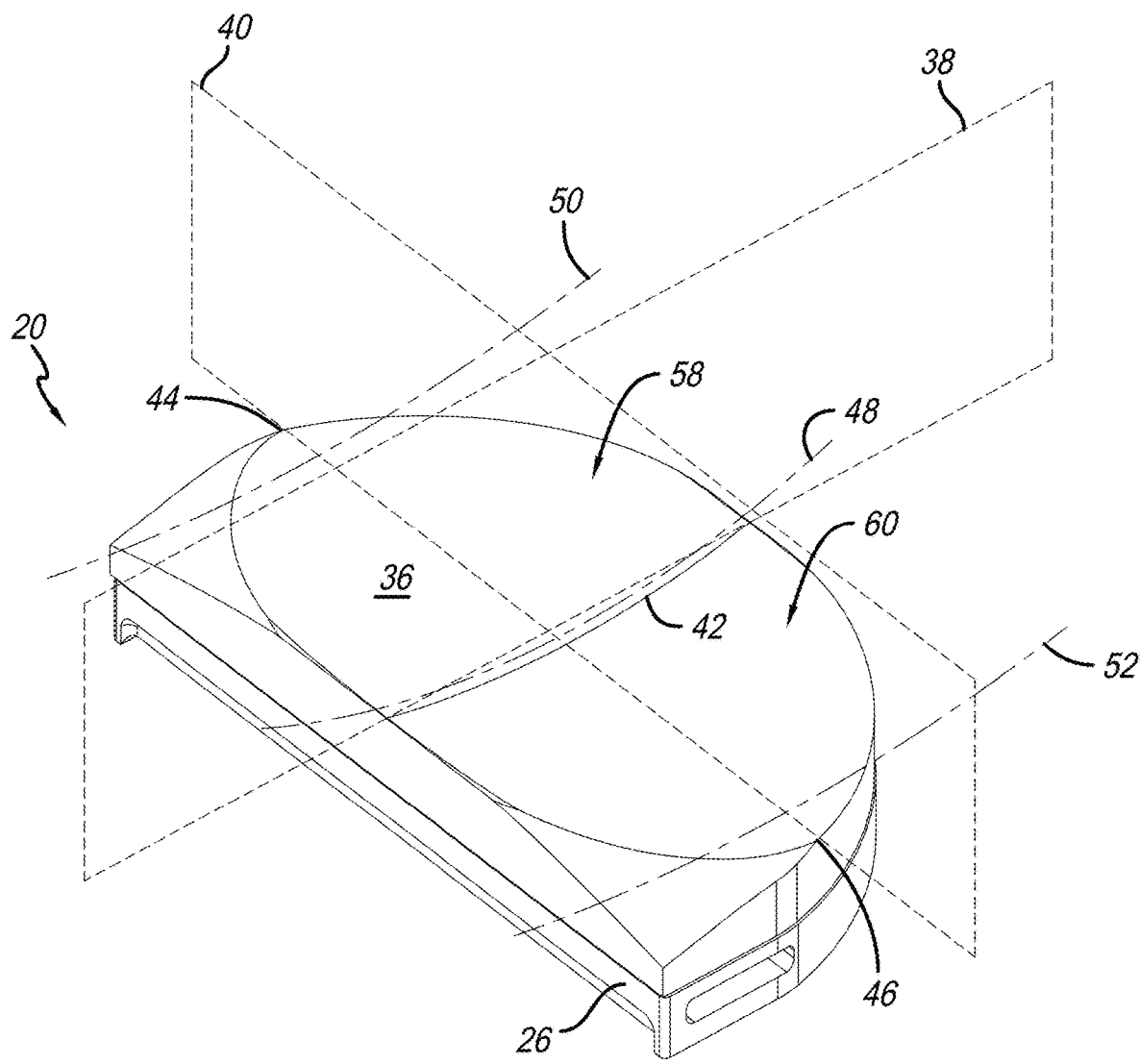
FIG. 4 is a perspective view of the tibial insert illustrated in FIGS. 2 and 3, further illustrating one embodiment where the variable articular surface has a lofted concave geometry.

In one embodiment, as best illustrated in FIGS. 2-4, the tibial insert 20 may be symmetrical about a coronal plane 38 and symmetrical about a median plane 40 whereby the variable articular surface 36 is also symmetrical about both the coronal plane 38 and the median plane 40. In this embodiment, the symmetrical variable articular surface 36 facilitates implantation with either of the lateral or medial condyles 28, 28' in either of the right knee as part of a right unicompartmental knee replacement or the left knee as part of a left unicompartmental knee replacement. As such, the underlying tibial baseplate 26 to which the tibial insert 20 couples is of a geometry that allows the tibial insert 20 to couple thereto regardless whether the tibial baseplate 26 is underneath the lateral or medial condyles 28, 28' in either the right knee or the left knee. As such, in one embodiment, the tibial insert 20 may be of a singular design usable with any one of the four condyles of the human knees.

For example, FIG. 1 illustrates the tibial insert 20 and the tibial baseplate 26 implanted into the patient tibia 34 for use in providing support underneath the condyle 28. In embodiments wherein the patient femur 30 and the patient tibia 34 illustrated in FIG. 1 are from the left leg, the tibial insert 20 attached to the tibial baseplate 26 would be considered implanted on a lateral side of the left knee. Rotating the tibial baseplate 26 by 180 degrees and coupling the tibial insert 20 thereto permits implantation into the patient tibia 34 below the condyle 28', which would be considered implanted on a medial side of the left knee in this example. Reciprocally, when the patient femur 30 and the patient tibia 34 illustrated in FIG. 1 are from the right leg, the tibial baseplate 26 and the tibial insert 20 attached thereto would be considered implanted on a medial side of the right knee. Similarly, rotating the baseplate 26 by 180 degrees and coupling the tibial insert 20 thereto permits implantation into the patient tibia 34 below the condyle 28', which would be considered implanted on a lateral side of the right knee in this second example. In each of these four configurations, the symmetrical nature of the variable articular surface 36 effectively provides the same geometric surface upon which the curved articular surface 32 of the femoral component 24 may articulate.

As such, the geometry of the tibial insert 20 and the tibial baseplate 26 are effectively compatible for use in any unicompartmental knee replacement surgery, namely the two condyles in the right knee or the two condyles in the left knee. The symmetry of the variable articular surface 36 thus ensures compatibility with both condyles in the right and left knees regardless of the orientation the tibial insert 20 is implanted. Such compatibility effectively decreases the quantity of the tibial inserts 20 and the quantity of tibial baseplates 26 that a hospital or surgery center needs to stock to perform unicompartmental knee surgery. In effect, the tibial insert 20 and/or the tibial baseplate 26 in these embodiments could reduce inventory costs up to 75% compared to traditional asymmetrical orthopedic implants. To this end, in this embodiment, only one set of the tibial insert 20 and the tibial baseplate 26 are needed per size.

The femoral component 24 and the tibial baseplate 26 may affix to the respective patient femur 30 and the patient tibia 34 by methods well known in the art, such as bone cement or the like. Moreover, the tibial baseplate 26 is designed to selectively receive and retain the tibial insert 20 so the femoral component 24 may articulate relative thereto after implantation. In this respect, the tibial insert 20 may couple to the tibial baseplate 26 by way of cemented or cementless designs known in the art, such as, but not necessarily limited to, adhesives, snap-fit engagement, threaded screw(s) or bolt(s), locking cross pin(s), metal clip(s), or other couplings known in the art. In one embodiment, the adhesive may be a bone cement (e.g., polymethylmethacrylate (PMMA) or the like), a fibrin adhesive, a collagen adhesive, a polyurethane adhesive, an epoxy resin adhesive, cyanoacrylates, polyesters, or zinc polycarboxylate.

Figure 5:
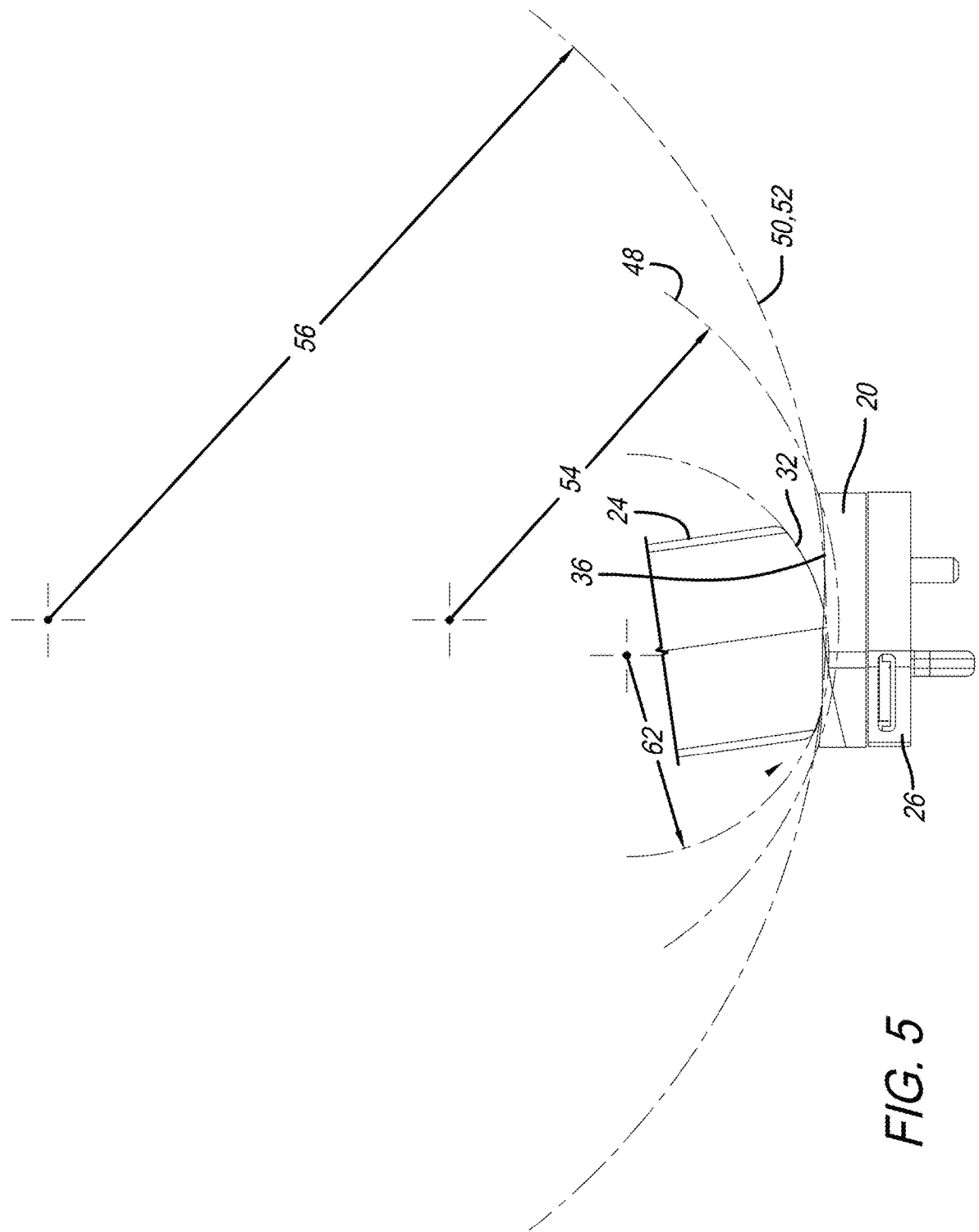
FIG. 5 is an end view of the tibial insert illustrated in FIGS. 2-4, illustrating one embodiment where the variable articular surface has a centerline curvature relatively smaller than a distal curvature, both of which are relatively larger than a curved articulating surface of the femoral component.

FIGS. 3-5 illustrate one embodiment wherein the variable articular surface 36 has a medial-to-lateral cross-section in the form of a circular curvature (best illustrated in FIG. 5), the size of which generally increases when progressively moving from a centerline 42 to each of a pair of edges 44, 46. In this embodiment, because the tibial insert 20 and the variable articular surface 36 are symmetrical, either of the edges 44, 46 could be construed as an anterior edge or a posterior edge, and the correct anatomical reference will ultimately depend on the orientation of the tibial insert 20 after implantation. Moreover, of course, the curvature of the variable articular surface 36 could be other non-geometric shapes (e.g., a trough shape, as discussed in more detail below with respect to FIGS. 17-21) or geometric shapes such as that of a parabolic curve, an elliptical curve, or a spline curve, etc.

By way of example, and to highlight the features of the variable articular surface 36, FIGS. 3 and 4 demark curvatures along the length of the tibial insert 20, and the radii of those curvatures are more specifically illustrated in FIG. 5. In this respect, a centerline curvature 48 is taken about the centerline 42, and a pair of distal curvatures 50, 52 are taken about reciprocal locations respectively proximal the edges 44, 46. As such, the end view of FIG. 5 illustrates that the centerline curvature 48 has a centerline radius 54 that is relatively smaller than a distal radius 56 of either of the distal curvatures 50, 52 positioned between the centerline 42 and either of the edges 44, 46. In this respect, the radius of curvature of the variable articular surface 36 progressively gets larger when viewed from the medial-to-later frontal cross-section when moving anteriorly/posteriorly away from the centerline 42 toward each of the edges 44, 46. As such, FIG. 5 illustrates that the distal radius 56 of the distal curvatures 50, 52 are larger and less constraining than the centerline radius 54 of the centerline curvature 48.

As such, the cross-section radius of the concave structure of the variable articular surface 36 varies when moving within the frontal plane away from the coronal plane 38 on either side of the centerline 42 toward each of the edges 44, 46. This effectively forms a pair of symmetric lofted concave surfaces 58, 60 on each side of the centerline 42 that, when considered in combination, essentially form the entirety of one embodiment of the variable articular surface 36. The pair of symmetric lofted concave surfaces 58, 60 accommodate a range of internal and external rotations of the femoral component 24 between extension and flexion positions while maintaining a relatively constant contact patch between the curved articular surface 32 of the femoral component 24 and the variable articular surface 36 of the tibial insert 20, as illustrated in more detail below with respect to FIGS. 6-11. This permits the femoral component 24 to move between extension and flexion while simultaneously allowing for ±10 degrees of internal or external rotation of the femoral component 24 relative to the tibial insert 20.

Figure 10:
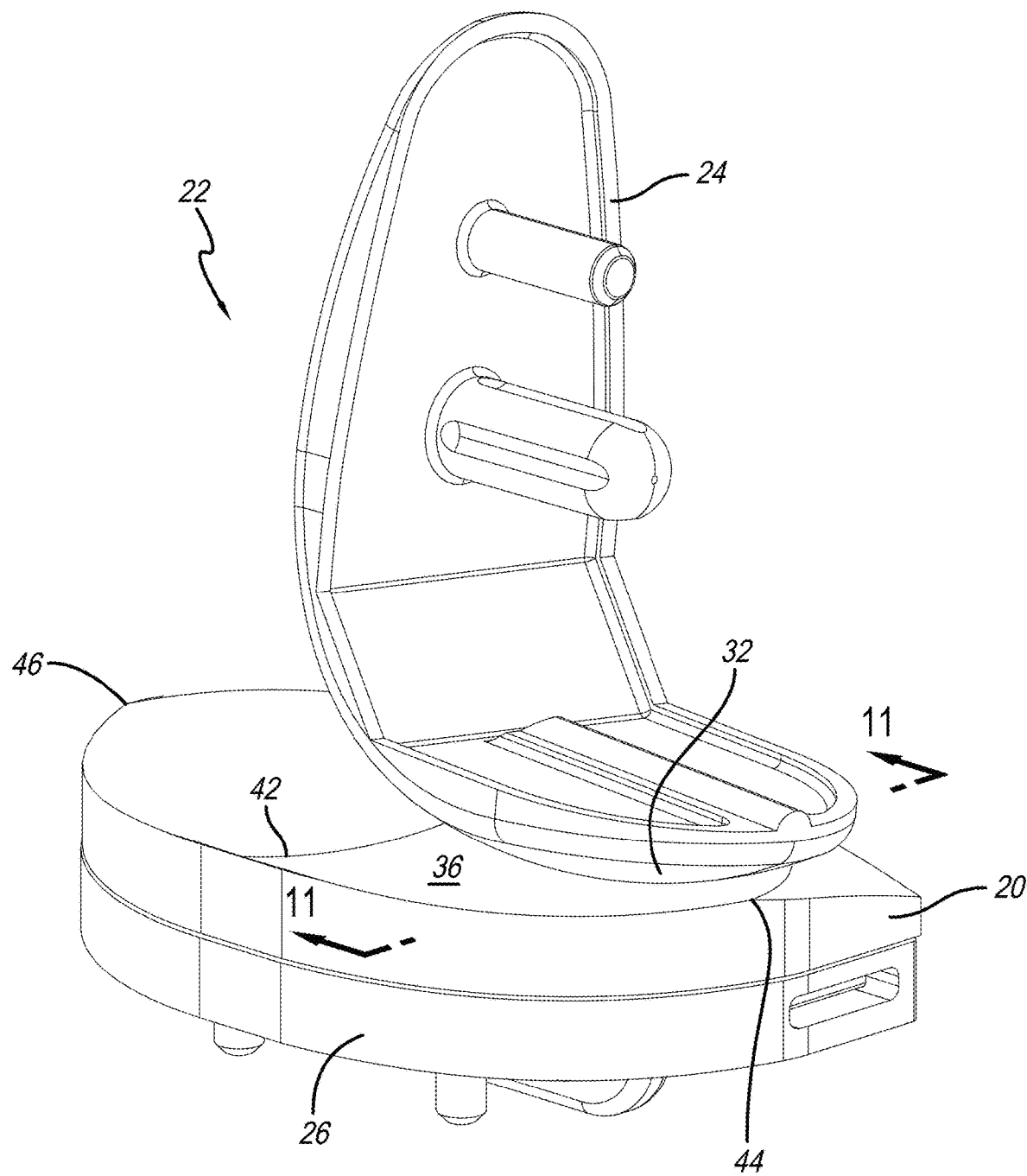
FIG. 10 is a perspective view of the unicompartmental knee replacement with the femoral component in the flexion position relative to the tibial insert.
Figure 11:
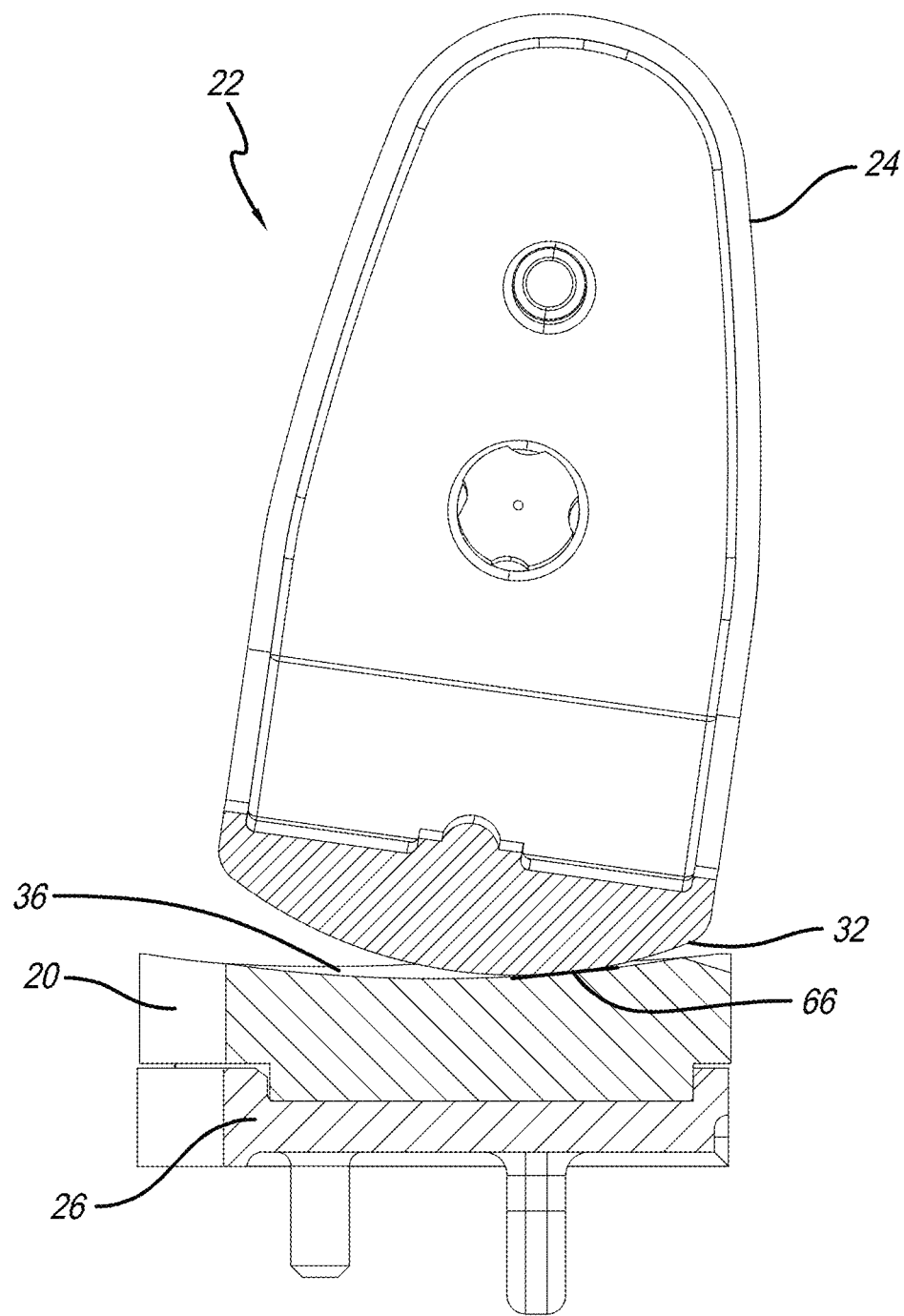
FIG. 11 is a cross-sectional view taken about the line 11-11 in FIG. 10, further illustrating the curved articulating surface of the femoral component seated on the variable articular surface of the tibial insert in a relatively less constrained position than when in the extension position illustrated in FIG. 7 and in a relatively less constrained position than when in the intermediate position illustrated in FIG. 9.

FIG. 5 also illustrates that the curved articular surface 32 of the femoral component 24 includes an articular surface radius 62 relatively smaller than the centerline radius 54 and relatively smaller than any radius along the variable articular surface 36 between the centerline 42 and the edges 44, 46, including the distal radius 56 of the distal curvatures 50, 52. In this embodiment, the curved articular surface 32 of the femoral component 24 has a constant frontal plane geometry while the curvature of the variable articular surface 36 changes along the frontal plane when moving from the centerline 42 to each of the edges 44, 46. As such, the ratio of the radius of the curved articular surface 32 of the femoral component 24 to that of the variable articular surface 36 changes when moving the unicompartmental knee replacement 22 from extension (e.g., as illustrated in FIGS. 6 and 7) to flexion (e.g., as illustrated in FIGS. 10 and 11).

Specifically, the progressively increasing size of the radius of curvature within each of the lofted concave surfaces 58, 60 allows for progressively less constraint of the femoral component 24 during flexion/rollback in either the left knee or the right knee relative to the constraint near the centerline 42 when the unicompartmental knee replacement 22 is in extension. This is the result of the concave geometry of the variable articular surface 36 having a progressively larger medial-to-lateral frontal cross-section opening when moving from the centerline 42 to each of the edges 44, 46 in this embodiment. In effect, the curved articular surface 32 of the femoral component 24 has less room to move within the relatively smaller medial-to-lateral frontal cross-section opening of the variable articular surface 36 near the centerline 42 (i.e., there is more congruence between the curved articular surface 32 of the femoral component 24 and the variable articular surface 36 of the tibial insert 20 when in extension) and has progressively more room to move within the progressively larger medial-to-lateral frontal cross-section opening of the variable articular surface 36 within the frontal plane as the femoral component 24 moves away from the centerline 42 from extension to flexion, i.e., the femoral component 24 becomes progressively less constrained with the tibial insert 20.

In one embodiment, a congruence ratio between the articular surface radius 62 of the femoral component 24 and the centerline radius 54 of the tibial insert 20 may be approximately 1:2.5 at full extension (i.e., zero degrees of flexion). The congruence ratio may then progressively change when moving along the length each of the lofted concave surfaces 58, 60 from the centerline 42 to each of the edges 44, 46 as the femoral component 24 progressively articulates from full extension (i.e., zero degrees of flexion) to ninety degrees of flexion. In one embodiment, the congruence ratio between the articular surface radius 62 of the femoral component 24 and the distal radius 56 may be as high as approximately 1:5 near one or both of the edges 44, 46. The result is that the femoral component 24 is initially relatively more constrained when in full extension, but becomes progressively less constrained when moving into the flexion/rollback position. This allows the femoral component 24 to progressively move farther off the median plane 40, such as along a path 64 illustrated in FIG. 3, to better mimic natural knee kinematics, such as helping eliminate an increase in loading due to posterior cruciate ligament ("PCL") and/or soft tissue axial forces during flexion/rollback. Moreover, such contact ratios allow for flatter, but not flat, posterior contact to limit the possibility of anterior lift while providing lateral support and a non-vertical positioning of the femoral component 24. In this embodiment, the structure of the lofted concave surfaces 58, 60 results in the variable articular surface 36 being relatively more lofted closer to each of the edges 44, 46 relative to the centerline 42 to support use of the tibial insert 20 as both a medial or lateral component in both left or right knee applications because of the medial-lateral conformity. The structure of the lofted concave surfaces 58, 60 results in variable medial-to-lateral constraint, wherein the constraint between the tibial insert 20 and the femoral component 24 decreases as the femoral component 24 rolls back when the knee moves from extension (FIGS. 6-7) to flexion (FIGS. 10-11).

Figure 6:
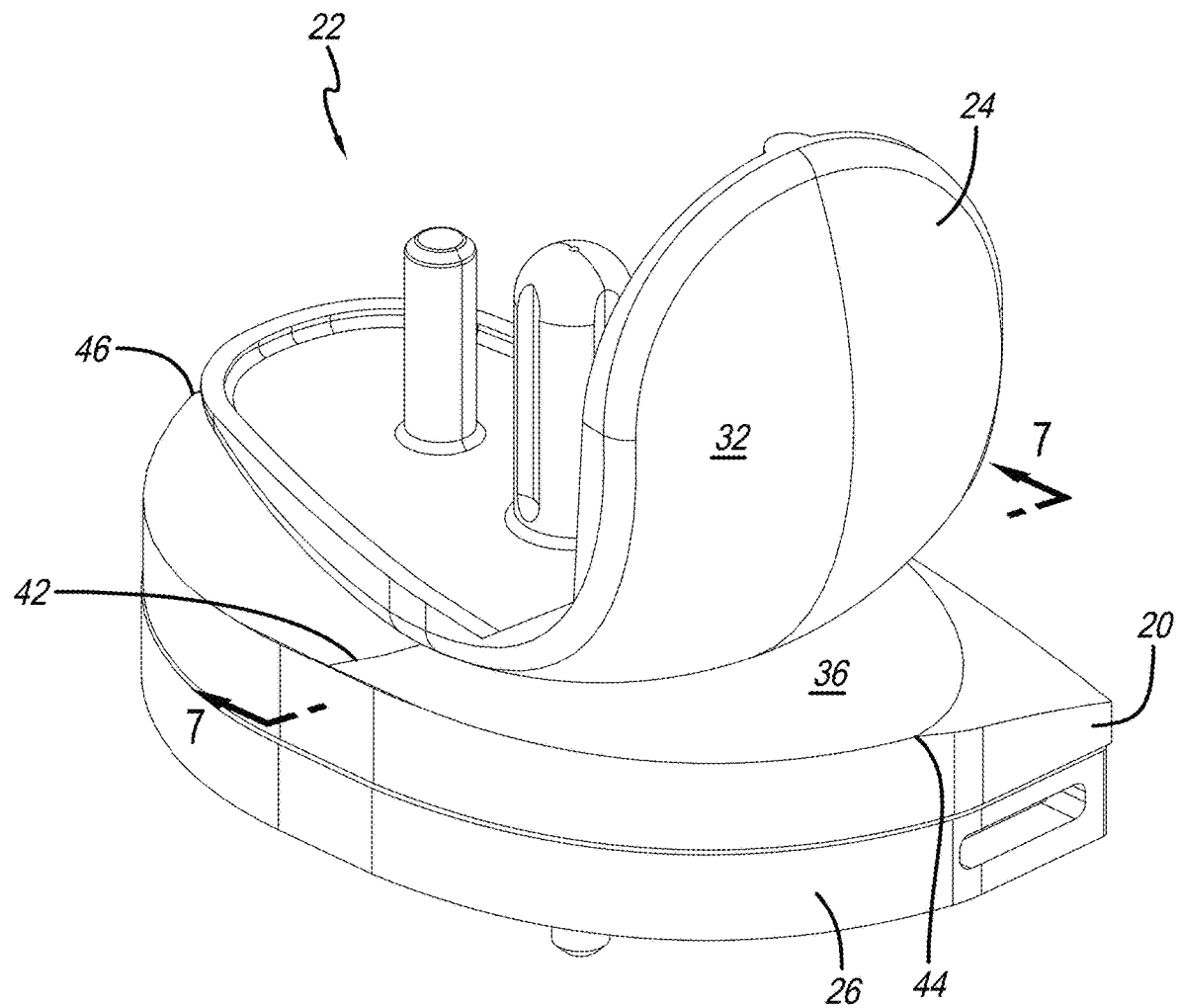
FIG. 6 is a perspective view of the unicompartmental knee replacement with the femoral component in the extension position relative to the tibial insert.
Figure 7:
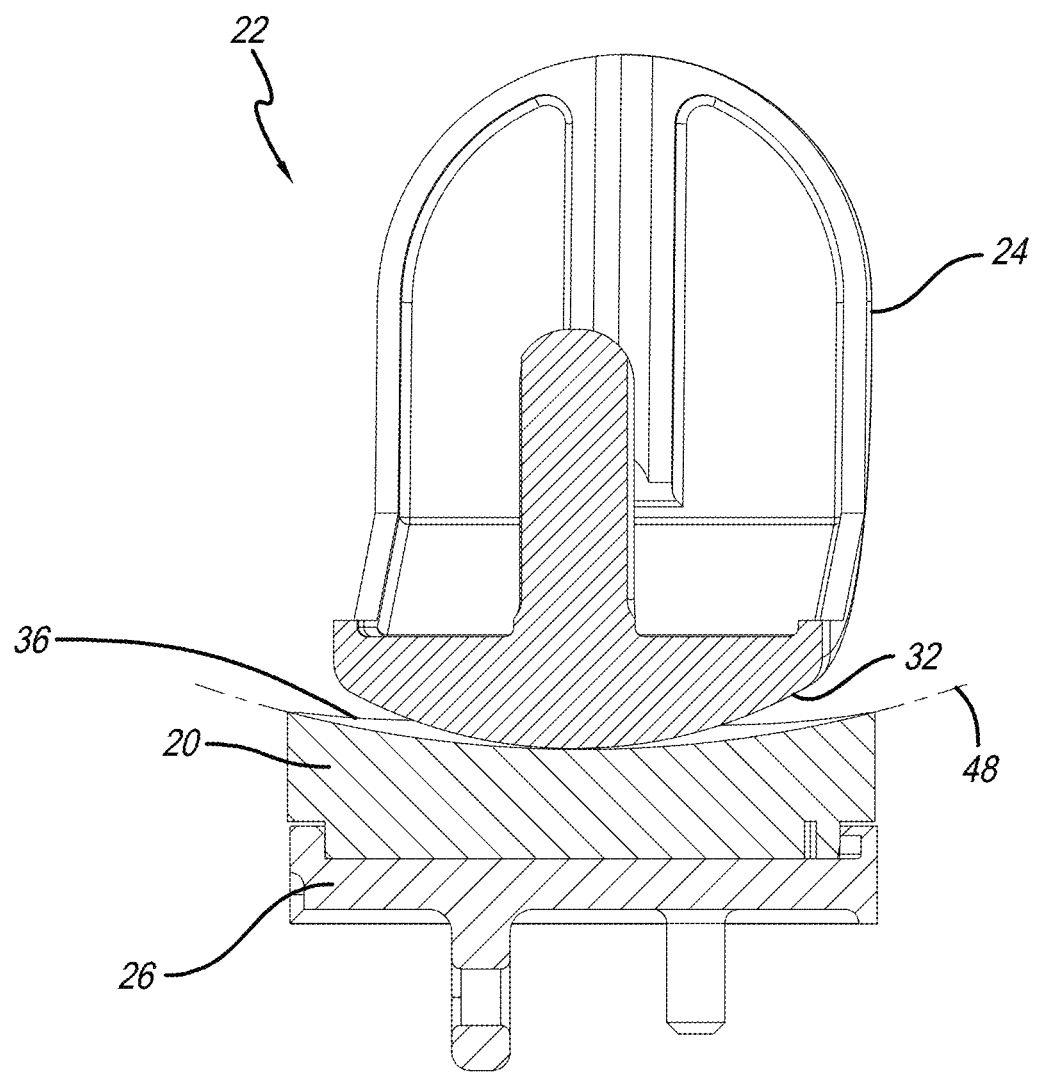
FIG. 7 is a cross-sectional view taken about the line 7-7 in FIG. 6, further illustrating the curved articulating surface of the femoral component seated on the variable articular surface of the tibial insert when the femoral component is in the extension position.
Figure 8:
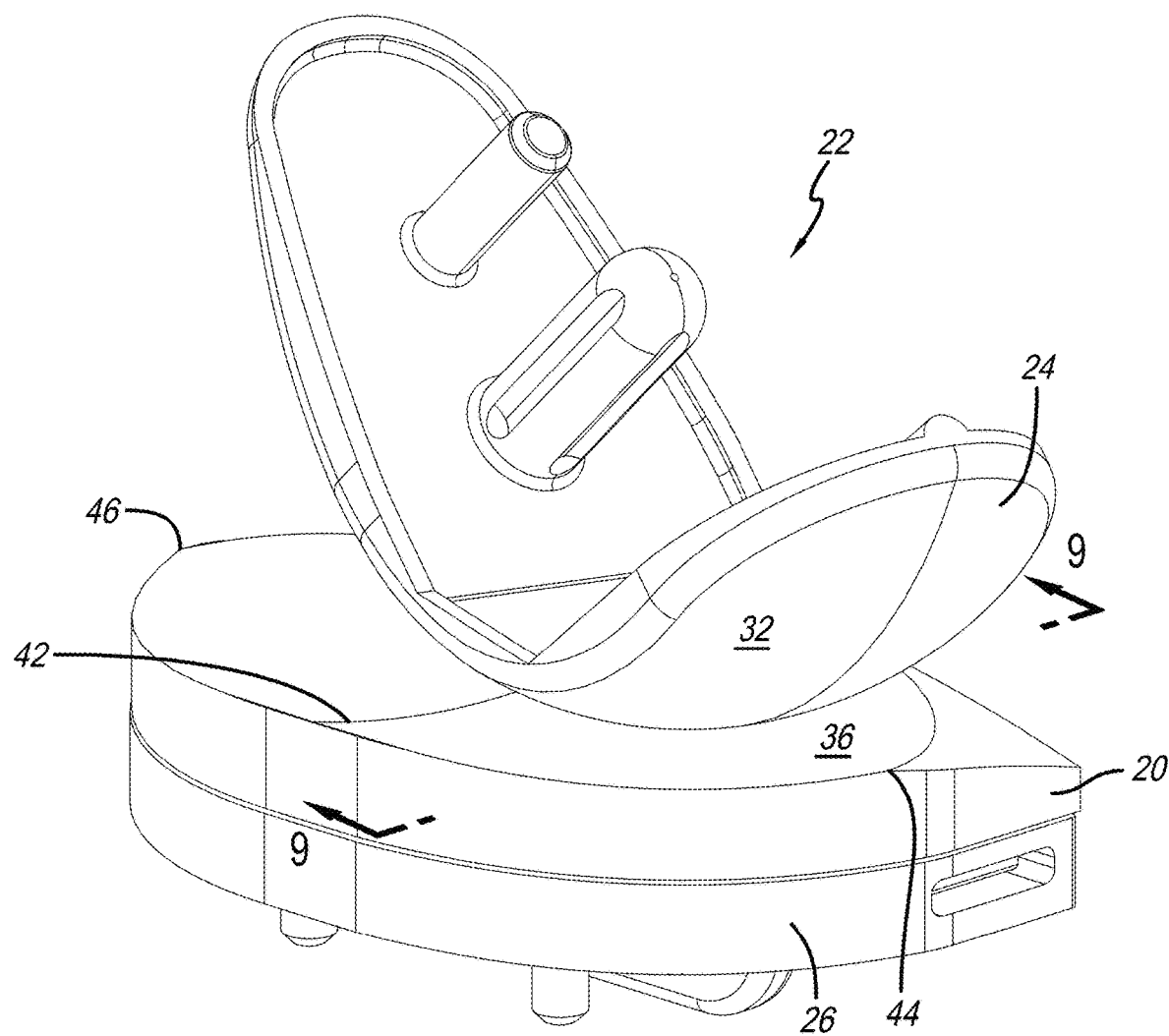
FIG. 8 is a perspective view of the unicompartmental knee replacement similar to FIG. 6, with the femoral component in an intermediate position between the extension position and the flexion position.
Figure 9:
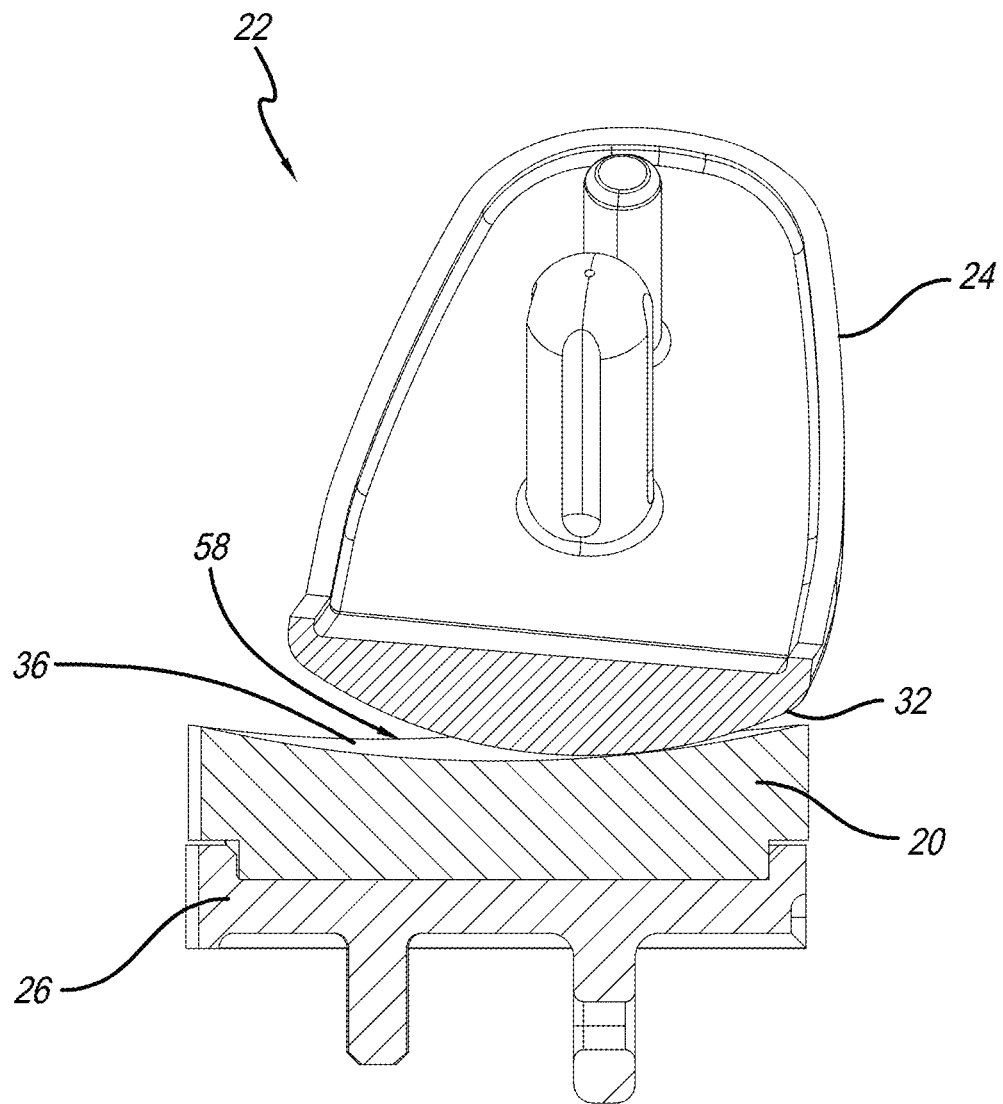
FIG. 9 is a cross-sectional view taken about the line 9-9 in FIG. 8, further illustrating the curved articulating surface of the femoral component seated on the variable articular surface of the tibial insert in a relatively less constrained position than when in the extension position illustrated in FIG. 7.

More specifically, e.g., FIG. 6 is a perspective view illustrating the femoral component 24 of the unicompartmental knee replacement 22 in full extension (i.e., zero degrees of flexion). The cross-sectional view of FIG. 7 illustrates that the curved articular surface 32 of the femoral component 24 is relatively constrained within the centerline curvature 48 of the variable articular surface 36. Due to natural knee kinematics, the femoral component 24 is somewhat off center relative to the tibial insert 20 when in this full extension or zero degrees flexion position. FIG. 8 illustrates initial rotation of the unicompartmental knee replacement 22 from the full extension position illustrated in FIG. 6. Here, the cross-sectional view of FIG. 9 more specifically illustrates that the curved articular surface 32 remains in contact with the variable articular surface 36 within the lofted concave surface 58, while at the same time continuing to rotate off center relative to the tibial insert 20, e.g., such as along the path 64 illustrated in FIG. 3.

Accordingly, FIG. 10 illustrates the unicompartmental knee replacement 22 in full flexion (i.e., 90 degrees rotation), and the cross-sectional view of FIG. 11 illustrates that the curved articular surface 32 of the femoral component 24 continues to remain in contact with the variable articular surface 36 along a contact patch 66, instead of a point load. Here, the femoral component 24 is further offset relative to the tibial insert 20 and the tibial baseplate 26, which the structure of the lofted concave surfaces 58, 60 permit as a result of the variable articular surface 36 providing less constraint when in this flexion position relative to the full extension position. Additionally, the concave curvature of the variable articular surface 36 in the frontal plane parallel to the coronal plane 38, versus the curvature along the median plane 40, interacts with the constant curved articular surface 32 of the femoral component 24 to resist posterior rotational moment. This helps prevent failure of fixation caused by anterior lift-off of the tibial baseplate 26. In alternative embodiments, spline or higher-order curvature definitions could create curvatures with similar results that prevent said lift-off. This, as mentioned above, allows the femoral component 24 to move between extension and flexion while simultaneously allowing for ±10 degrees of internal or external rotation relative to the tibial insert 20.

Figure 12:
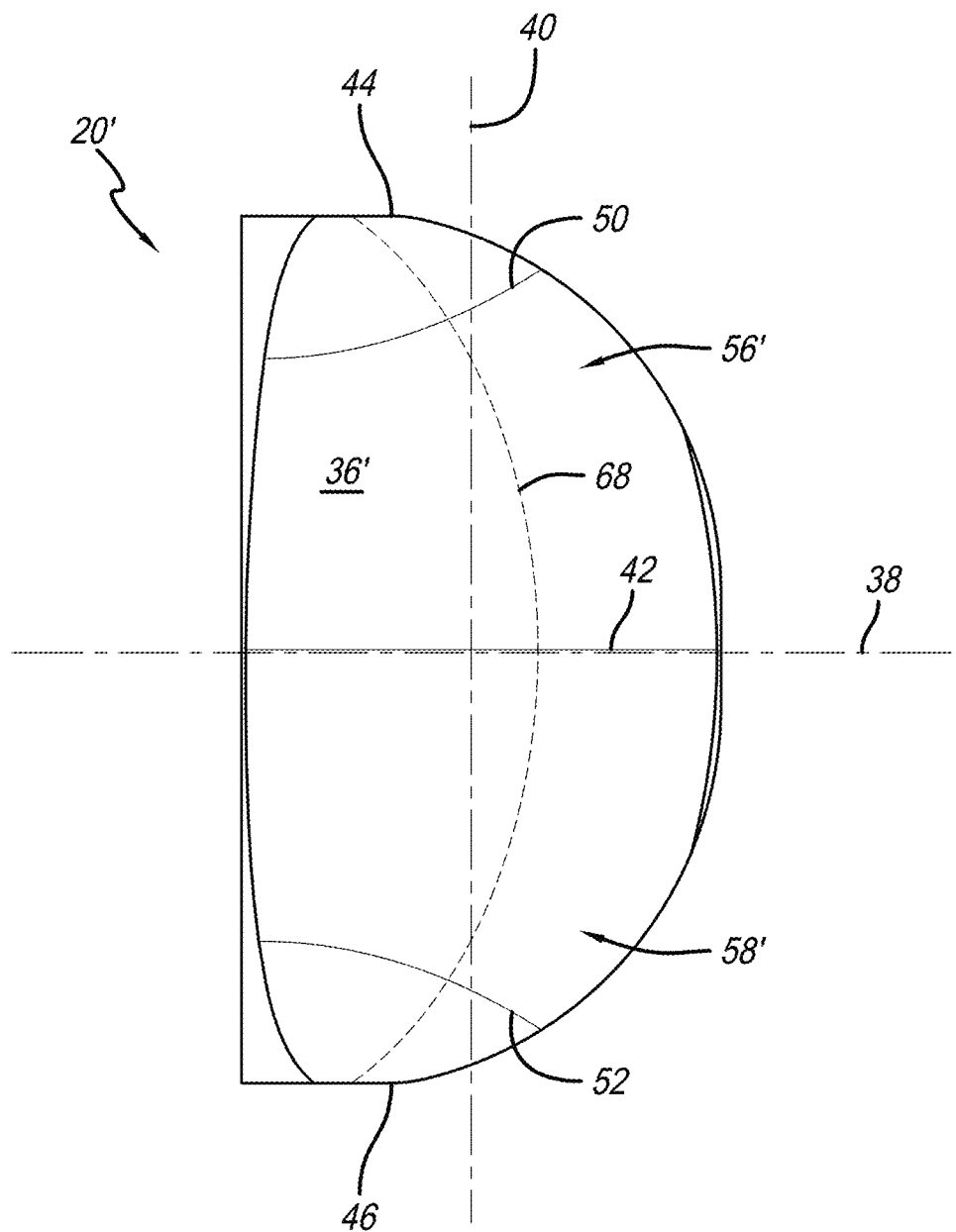
FIG. 12 is a top plan view of an alternative embodiment of the tibial insert having a partially symmetrical variable articular surface symmetrical about the coronal plane and asymmetric about the median plane.
Figure 13:
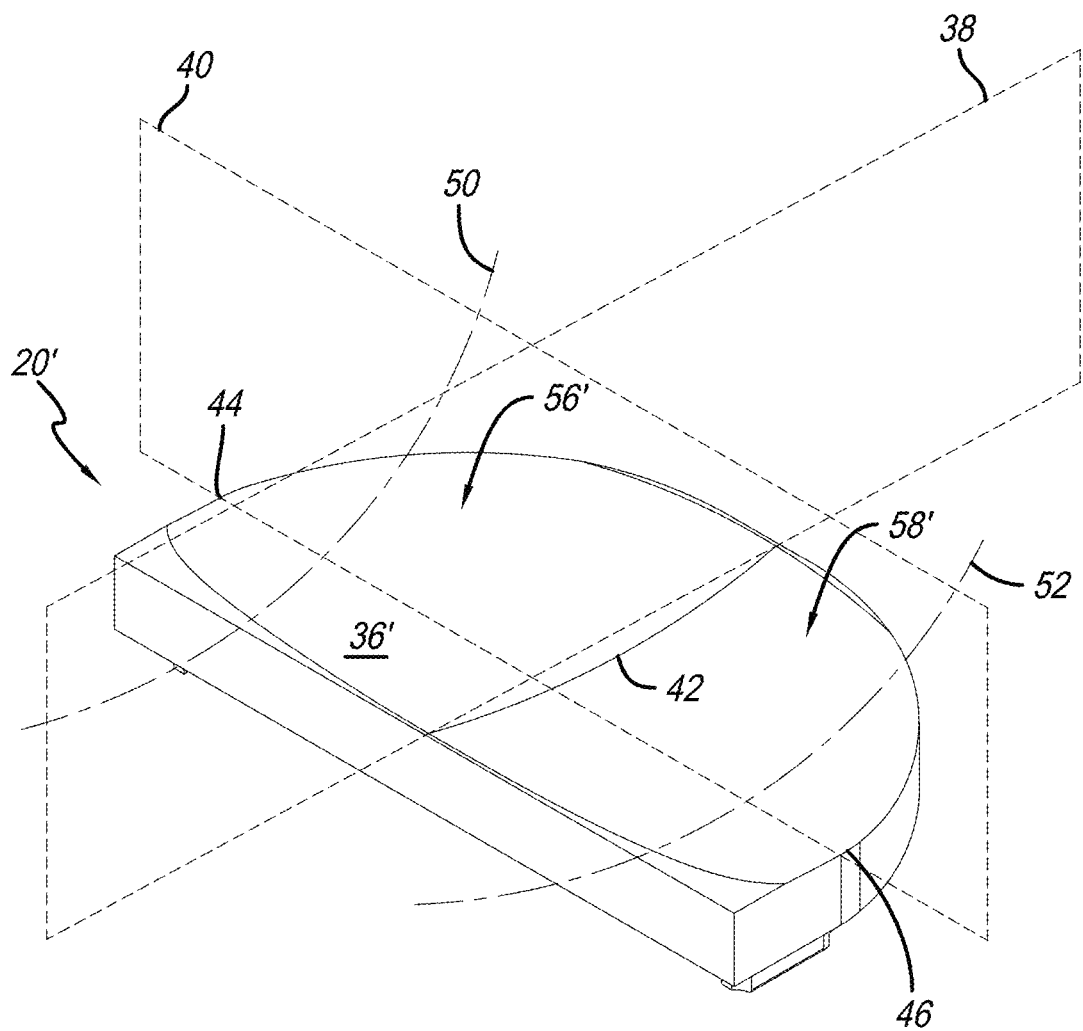
FIG. 13 is a perspective view of the alternative tibial insert of FIG. 12, further illustrating the partially symmetrical variable articular surface being symmetrical about the coronal plane and asymmetrical about the median plane.

Additionally, FIGS. 12 and 13 illustrate an alternative embodiment where an alternative variable articular surface 36' of an alternative tibial insert 20' is symmetrical about the coronal plane 38, while being asymmetrical about the median plane 40. Here, the distal curvature 50 proximal the edge 44 is somewhat offset (best illustrated in FIG. 12) from otherwise being generally aligned with the centerline 42 (e.g., contrast with FIG. 3). The distal curvature 52 proximal the edge 46 is offset from the centerline 42 in a similar manner, and in a reciprocal or mirrored relationship relative to the distal curvature 50 proximal the edge 44, to maintain symmetry about the coronal plane 38. Accordingly, each of the lofted concave surfaces 56', 58' have a somewhat different geometry than the lofted concave surfaces 56, 58 discussed above (e.g., being asymmetrical bout the median plane 40), but remain reciprocally mirror images of one another about the coronal plane 38. In this embodiment, because the geometry of the lofted concave surfaces 56', 58' are not symmetrical about the median plane 40, the femoral component 24 tracks differently across the alternative variable articular surface 36', such as along a curved path 64 off center from the median plane 40, but still symmetrical about the coronal plane 38. Even so, this embodiment is similar to the embodiment disclosed above with respect to FIGS. 3 and 4, namely the concavity of the alternative variable articular surface 36' becomes generally progressively larger in a medial-to-lateral frontal cross-section when moving from the centerline 42 to either of the edges 44, 46. As a result, the congruence of the curved articular surface 32 of the femoral component 24 with the alternative variable articular surface 36' still decreases as the femoral component 24 translates about the alternative variable articular surface 36' from the centerline 42 to either of the edges 44, 46.

Figure 14:
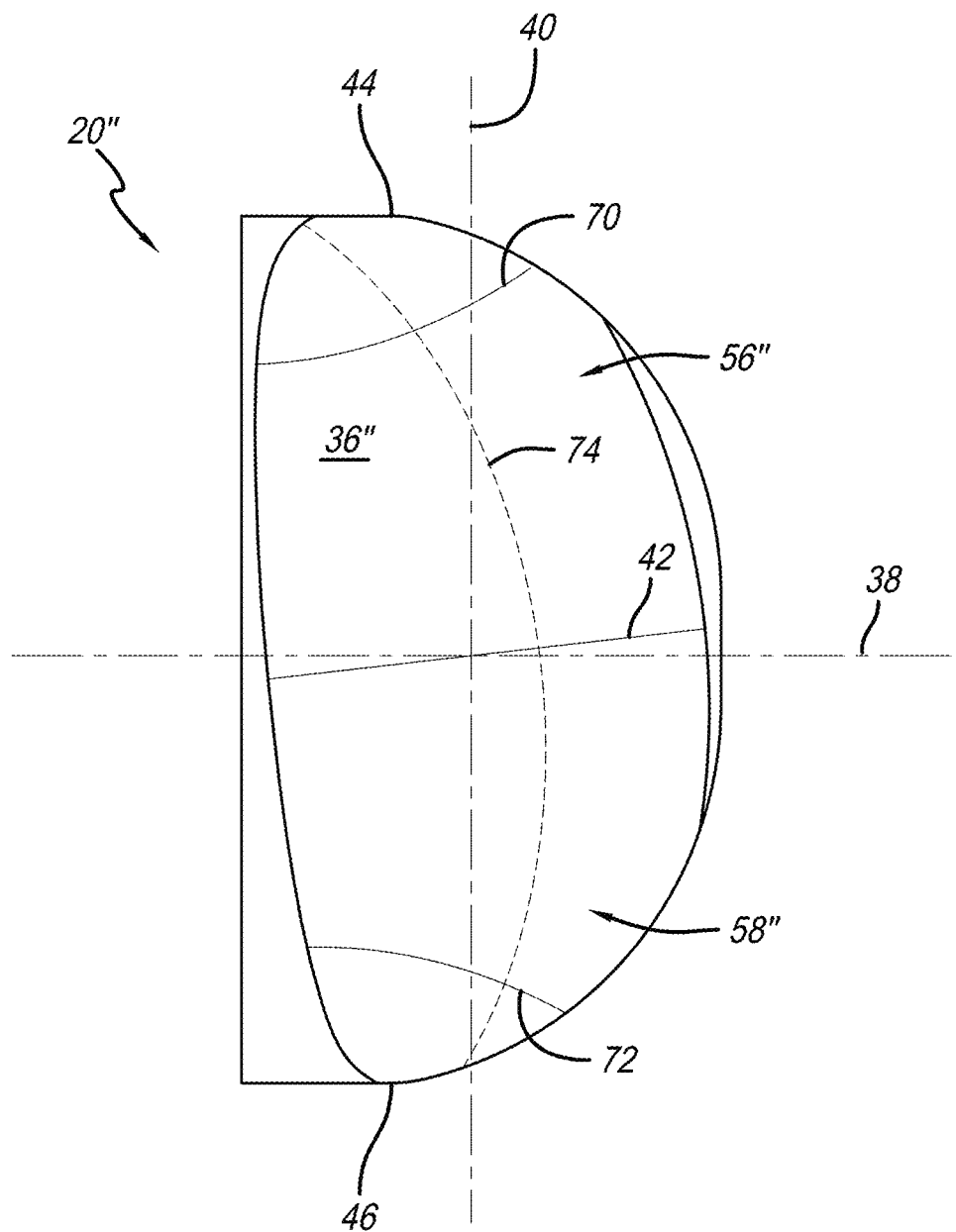
FIG. 14 is a top plan view of another alternative embodiment of the tibial insert having an asymmetrical variable articular surface.
Figure 15:
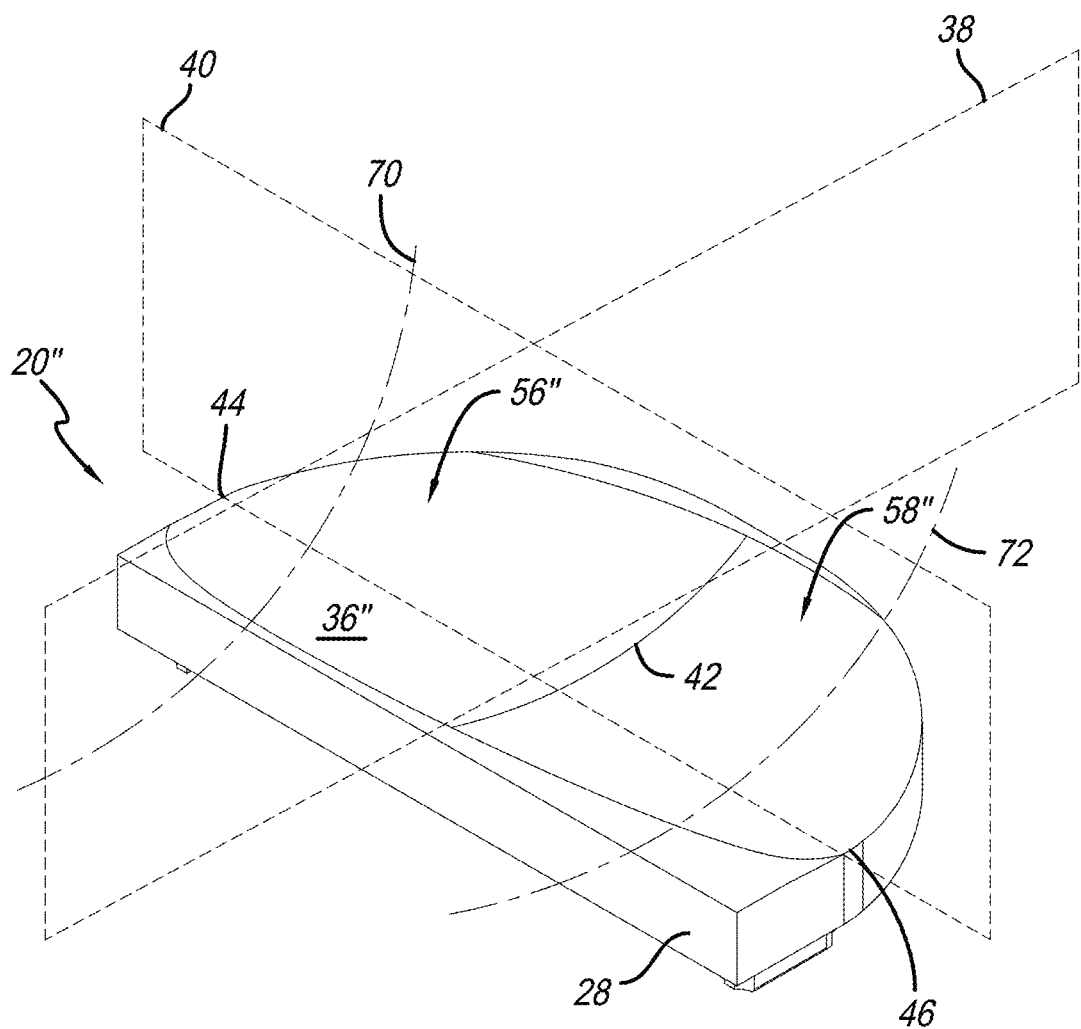
FIG. 15 is a perspective view of the alternative tibial insert of FIG. 14, further illustrating the asymmetry of the asymmetrical variable articular surface about both the coronal plane and the median plane.

FIGS. 14 and 15 illustrate another alternative embodiment of a tibial insert 20" wherein an alternative variable articular surface 36" is illustrated being asymmetrical about both the coronal plane 38 and the median plane 40. Here, unlike the embodiments disclosed above where the tibial inserts 20, 20' and the variable articular surfaces 36, 36' are symmetrical about at least the coronal plane 38 for purposes of enhanced compatibility (i.e., where a single component is implantable in connection with more than one of the condyles 28, 28' in either a right knee or a left knee unicompartmental knee replacement), the asymmetrical design illustrated in FIGS. 14 and 15 is more conventional such that the tibial insert 20" is condyle/knee specific. As such, the alternative tibial insert 20" illustrated in FIGS. 14 and 15 cannot simply be rotated 180° for universal compatibility, so it may not achieve the same efficiencies as some of the other embodiments disclosed herein. But, similar to the other embodiments disclosed herein, the variable articular surface 36" is still less constraining when the knee is in flexion than when in extension.

In this respect, FIGS. 14 and 15 illustrate the alternative tibial insert 20" in one orientation where the edge 44 is to an anterior side of the tibial insert 20" and the edge 46 is to a posterior side thereof. As such, the construction of the alternative variable articular surface 36" is somewhat different than the embodiments discussed above. Here, e.g., the concavity of the alternative variable articular surface 36" may become generally progressively larger along the entire length of the alternative tibial insert 20" from the anterior edge 44 to the posterior edge 46 in a medial-to-lateral frontal cross-section. As such, an anterior curvature 70 illustrated proximal the anterior edge 44 is relatively smaller than a posterior curvature 72 illustrated proximal the posterior edge 46. The same would also be true for the mirror image version of the alternative tibial insert 20".

Moreover, the anterior curvature 70 proximal the anterior edge 44 is best shown in FIG. 14 offset from both the coronal plane 38 and the median plane 40, and is relatively smaller than the posterior curvature 72. The posterior curvature 72 is also illustrated being offset from both the coronal plane 38 and the median plane 40, albeit in a non-mirrored or non-reciprocal relationship relative to the anterior curvature 70, and to a greater extent as a result of the alternative variable articular surface 36" becoming generally progressively larger in the medial-to-lateral frontal cross-section. As such, a curved path 74 of the alternative tibial insert 20" does not pass through where the coronal plane 38 intersects the median plane 40, nor is the curved path 74 symmetrical about the coronal plane 38 or the median plane 40.

Moreover, the geometries of each of the respective lofted concave surfaces 56", 58" have no symmetry relative to one another as a result of the asymmetry of the alternative tibial insert 20" and the asymmetry of the alternative variable articular surface 36". Although, similar to the embodiments disclosed above, the congruence of the curved articular surface 32 of the femoral component 24 with the alternative variable articular surface 36" still decreases when moving from extension to flexion, albeit along the entire length of the alternative tibial insert 20'" from the anterior edge 44 to the posterior edge 46. Although, in one alternative embodiment, the concavity of the alternative variable articular surface 36" may only become progressively larger in the medial-to-lateral frontal cross-section at least partially or entirely within a posterior half (e.g., between the coronal plane 38 and the posterior edge 46 illustrated in FIG. 14) when moving posteriorly away from the coronal plane 38 toward the posterior edge 46.

Figure 16:
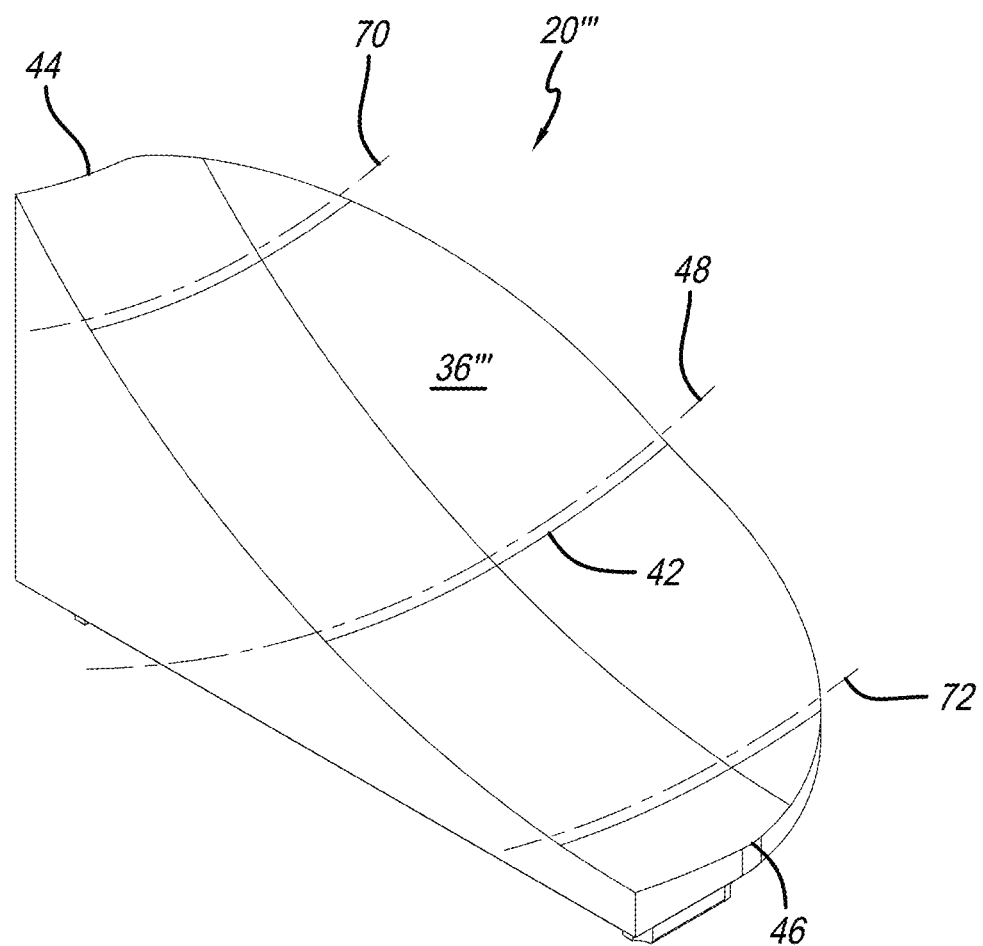
FIG. 16 is a perspective of another alternative embodiment of the tibial insert, further illustrating a semi-hemispherical variable articular surface.

FIG. 16 illustrates another alternative embodiment of a tibial insert 20'" where an alternative variable articular surface 36'" has a semi-hemispherical geometry. In this embodiment, the curvature or opening formed by the geometry of the alternative variable articular surface 36'" gradually enlarges in the medial-to-lateral frontal cross-section when moving at least partially or entirely along the length of the alternative tibial insert 20'", from the anterior edge 44 to the posterior edge 46. Specifically, e.g., the anterior curvature 70 proximal the anterior edge 44 has a relatively smaller radius or opening than the centerline curvature 48 at the centerline 42. Consistent therewith, the posterior curvature 72 has a relatively larger radius or opening than each of the centerline curvature 48 and the anterior curvature 70, whereby the tibial insert 20 is less constraining where the posterior curvature 72 is located than either of where the centerline curvature 48 or the anterior curvature 70 are located. In another embodiment, the concavity of the alternative variable articular surface 36'" may become progressively larger in the medial-to-lateral frontal cross-section at least partially or entirely within a posterior half (e.g., between the centerline 42 and the posterior edge 46 illustrated in FIG. 16) when moving posteriorly away from the centerline 42 toward the posterior edge 46.

Figure 17:
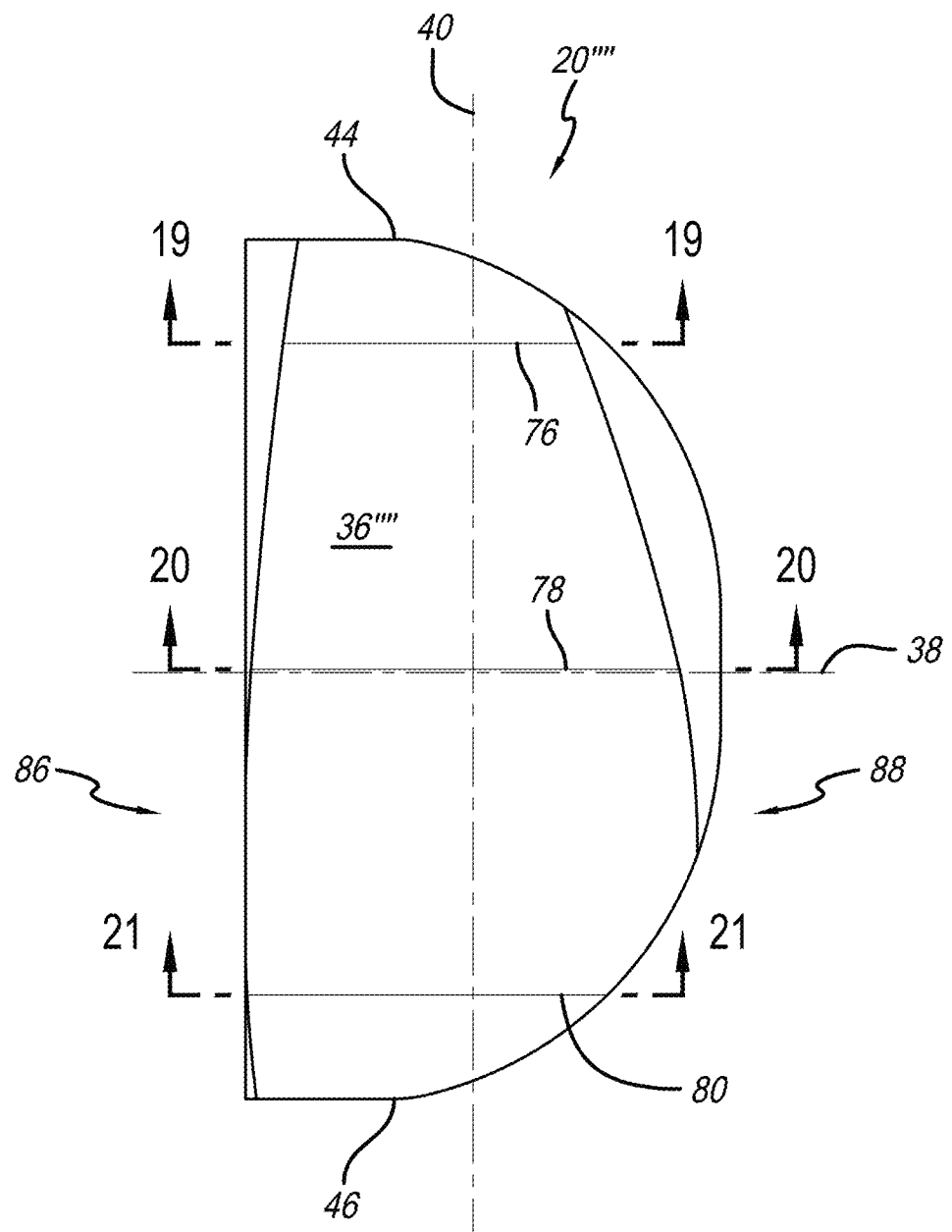
FIG. 17 is a top plan view of another embodiment of the tibial insert, further illustrating an alternative variable articular surface in the form of a concave trough.
Figure 18:
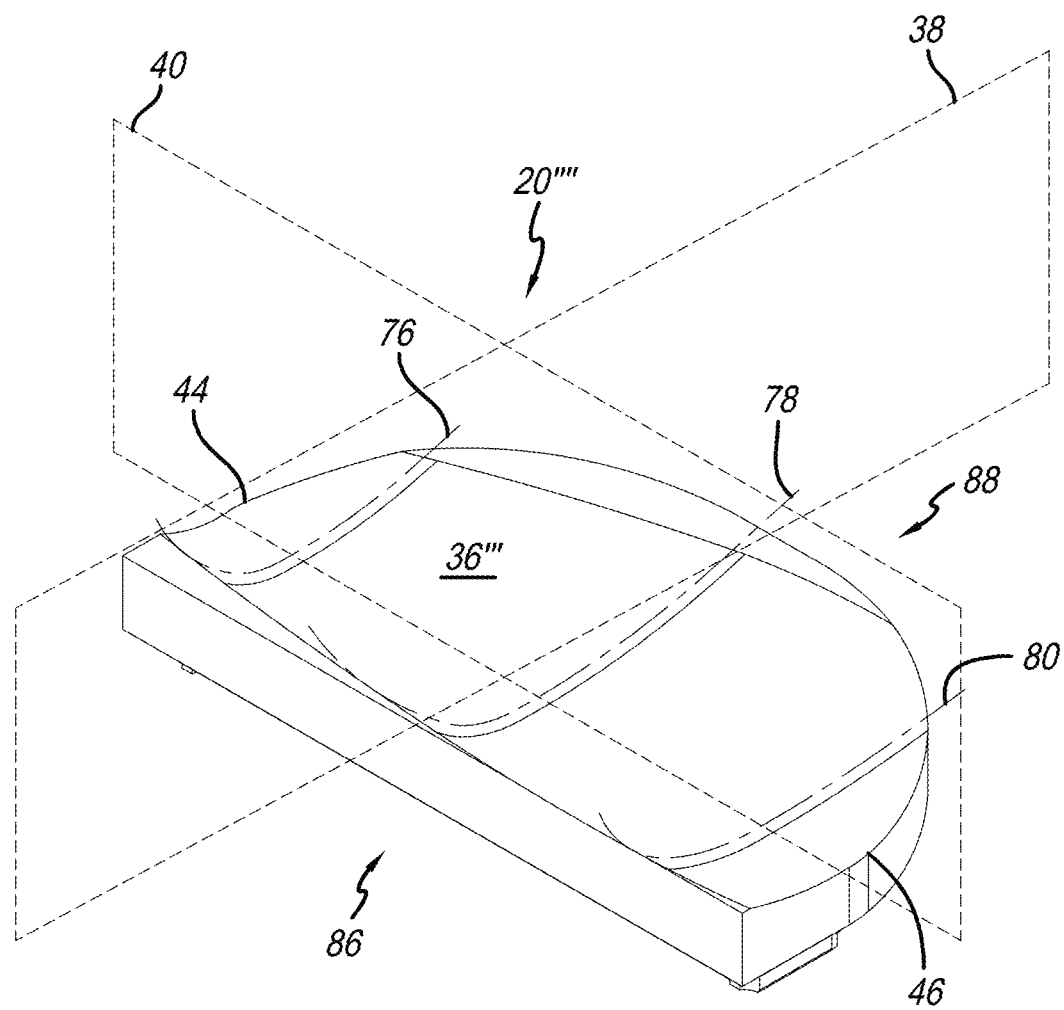
FIG. 18 is a perspective view of the alternative tibial insert of FIG. 17, further illustrating the concave trough generally progressively enlarging in a medial-to-lateral frontal cross-section anteriorly to posteriorly along a length of the tibial insert.
Figure 19:
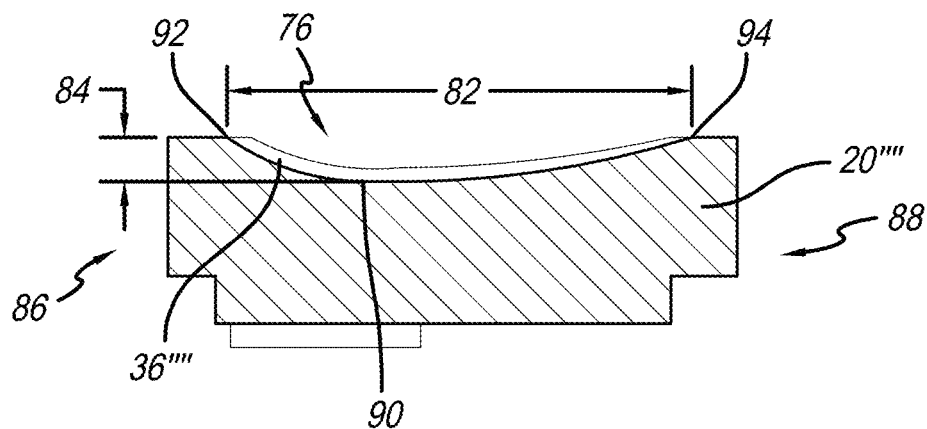
FIG. 19 is a cross-sectional view taken about the line 19-19 in FIG. 17, further illustrating the medial-to-lateral frontal cross-section of an anterior trough.
Figure 20:
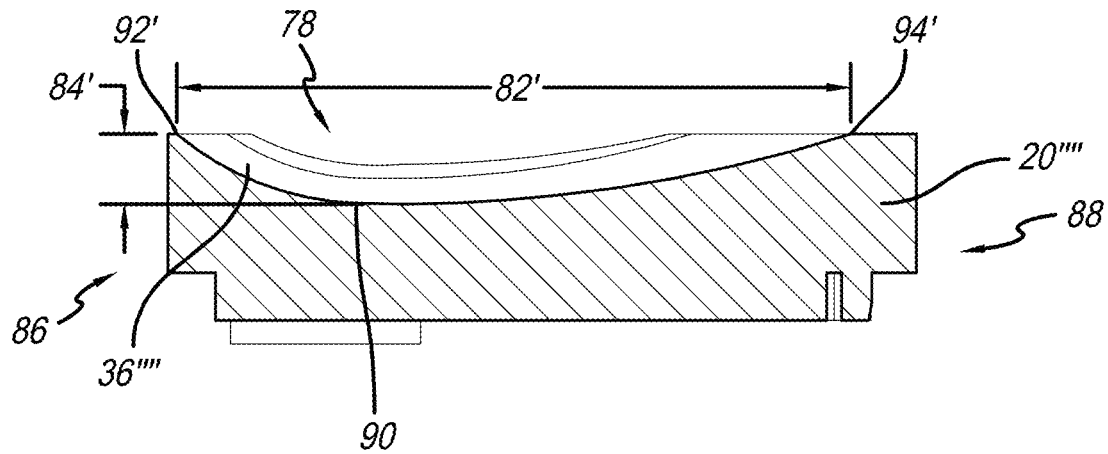
FIG. 20 is a cross-sectional view taken about the line 20-20 in FIG. 17, further illustrating the medial-to-lateral frontal cross-section of a central trough having a concave opening relatively less constraining than the concave opening of the anterior trough illustrated in FIG. 19.
Figure 21:
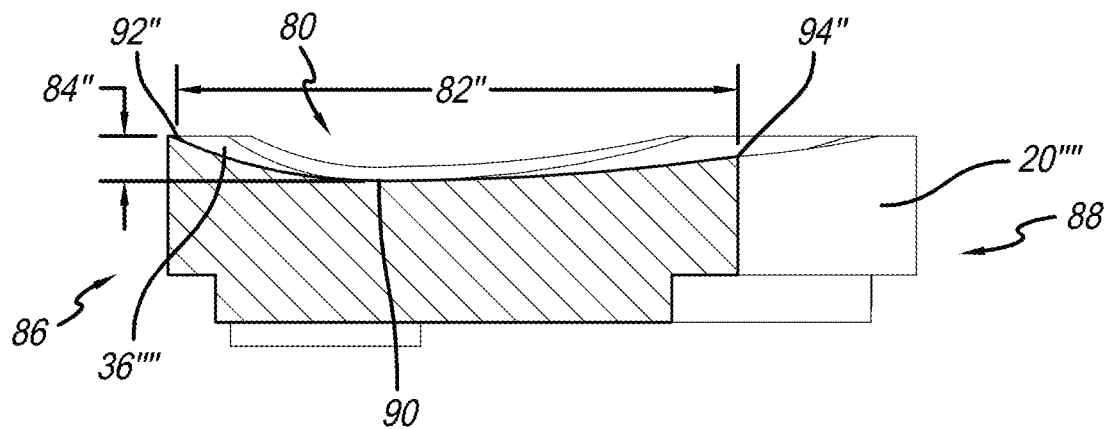
FIG. 21 is a cross-sectional view taken about the line 21-21 in FIG. 17, further illustrating the medial-to-lateral frontal cross-section of a posterior trough having a concave opening relatively less constraining than the concave opening of the anterior trough illustrated in FIG. 19 and relatively less constraining than the concave opening of the central trough illustrated in FIG. 20.

FIGS. 17 and 18 illustrate another alternative embodiment of a tibial insert 20"" having another alternative variable articular surface 36"" with a troughed concave geometry, and the cross-sectional views illustrated in FIGS. 19-21 are exemplary illustrations how the concavity of the variable articular surfaces 36, 36', 36", 36'", 36"" as disclosed herein may generally progressively become larger or otherwise widen in the medial-to-lateral frontal cross-section to decrease the congruence between any of the variable articular surfaces 36, 36', 36", 36'", 36"" and the curved articular surface 32 of the femoral component 24. In this respect, FIGS. 17 and 18 generally demark three locations where cross-sectional views illustrated in FIGS. 19-21 are taken to show an example how the geometry of the cross-section of the variable articular surface 36"" varies anteriorly to posteriorly. Specifically, e.g., FIG. 19 is a cross-section of the tibial insert 20"" near the location of an anterior trough 76 positioned generally within an anterior or upper half of the alternative tibial insert 20""; FIG. 20 is a cross-section of the tibial insert 20"" near the location of a central trough 78 positioned in about midway between the anterior edge 44 and the posterior edge 46; and FIG. 21 is a cross-section of the tibial insert 20"" near the location of a posterior trough 80 positioned generally within a posterior or lower half of the alternative tibial insert 20"". In this embodiment, the alternative tibial insert 20"" and the troughed variable articular surface 36"" are illustrated being asymmetrical about both the coronal plane 38 and the median plane 40, but the troughed variable articular surface 36"" could also be symmetrical about one or both of the coronal plane 38 and/or the median plane 40 in alternative embodiments, consistent with the embodiments disclosed herein.

In general, the cross-sectional views illustrated in FIGS. 19-21 illustrate the changing geometry of the troughed variable articular surface 36"" progressively from the anterior edge 44 to the posterior edge 46. In this respect, there are several characteristics that may change within the geometry of the variable articular surfaces 36, 36', 36", 36'", 36"" when moving anteriorly-to-posteriorly to decrease the congruence of the interaction of the curved articular surface 32 of the femoral component 24 with the respective variable articular surfaces 36, 36', 36", 36'", 36"", e.g., including the depth of the concavity of the variable articular surfaces 36, 36', 36", 36'", 36"", the height of the concavity of the variable articular surfaces 36, 36', 36", 36'", 36"", and/or the geometry near where the concavity of the variable articular surfaces 36, 36', 36", 36'", 36"" ends.

Specifically in this respect, the cross-sectional view of FIG. 19 illustrates one embodiment where the anterior trough 76 includes an opening 82 that is relatively smaller than an opening 82' where the cross-section of the central trough 78 is taken. The relatively wider opening 82' is less constraining because it permits more movement of the curved articular surface 32 of the femoral component 24 within the troughed variable articular surface 36''''. Furthermore, while the opening 82'' illustrated in FIG. 21 with respect to the cross-section of the posterior trough 80 is relatively smaller than the opening 82', but the surface geometry of the variable articular surface 36'''' at this cross-section is illustrated being less pronounced (i.e., flatter), meaning that the curved articular surface 32 of the femoral component 24 is able to move medial-to-lateral, and vice versa, with less constraint than when residing within the central trough 78 (and/or the anterior trough 76 for that matter), despite the opening 82'' being relatively smaller in width than the opening 82'.

In another aspect of these embodiments, a depth 84 of the concave variable articular surface 36'''' may also vary anteriorly to posteriorly, so long as the geometry facilitates decreasing the amount of congruence between the curved articular surface 32 of the femoral component 24 and the variable articular surface 36''''. Here, e.g., FIG. 19 illustrates that the depth 84 on a medial side 86 of the tibial insert 20'''' is relatively smaller than a depth 84' at the central trough 78, as illustrated in FIG. 20. But, as mentioned above, the opening 82' at the central trough 78 is relatively larger than the opening 82 at the anterior trough 76, whereby the additional depth 84' within the central trough 78 helps facilitate additional medial-to-lateral movement, and vice versa, of the curved articular surface 32 of the femoral component 24 within the troughed variable articular surface 36''''. FIG. 21 illustrates that a depth 84'' is relatively smaller than the depth 84' illustrated in FIG. 20 with respect to the central trough 78, but the posterior trough 80 is also still less congruent with the curved articular surface 32 of the femoral component 24 than the central trough 78, e.g., because the incline from a bottom or base 90'' of the concave surface illustrated therein to each of a medial transition lip 92'' and/or a lateral transition lip 94'' is relatively smaller (i.e., flatter) than that shown with respect to the incline from a bottom or base 90' of the central trough 78 to each of a medial transition lip 92' and/or a lateral transition lip 94'. Here, the relatively smaller or flatter incline allows for relatively more movement of the curved articular surface 32 of the femoral component 24 within the troughed variable articular surface 36'''', thereby achieving less congruence within the posterior trough 80 relative to the central tough 78.

Similarly, the degree of transition out from the respective troughs 76, 78, 80 at each of the medial transition lips 92, 92', 92'' and the lateral transition lips 94, 94', 94'' also affects the congruence between the curved articular surface 32 of the femoral component 24 and the applicable variable articular surface 36, 36', 36'', 36''', 36''''. For example, FIG. 19 illustrates a sharper or harder transition at each of the medial transition lip 92 and the lateral transition lip 94 relative to either of the medial transition lips 92', 92'' or the lateral transition lips 94', 94'' illustrated in FIG. 20 and FIG. 21. Here, the relatively sharper or steeper inclines at the transition lips 92, 94 facilitate retaining or "cupping" the curved articular surface 32 of the femoral component 24 within the confines of the concave geometry of the variable articular surface 36'''', i.e., this structural feature is more constraining. Flattening the transition at the lips 92, 94 (e.g., as best illustrated in FIG. 21 relative to FIGS. 19 and 20) allows for more movement of the curved articular surface 32 of the femoral component 24 within the concavity formed by the variable articular surface 36'''' for purposes of decreasing congruence. Of course, this feature and concept is also applicable to any of the variable articular surfaces 36, 36', 36'', 36''' disclosed herein.

As such, the cross-sectional views of FIGS. 19-21 are exemplary of how the curved articular surface 32 of the femoral component 24 becomes less constrained within the respective variable articular surfaces 36, 36', 36'', 36''', 36'''' when moving from extension to flexion, in accordance with the embodiments disclosed herein.

Of course, in alternative embodiments, the cross-sectional geometries of the openings 82, 84, 86 may be defined by something other than a trough, such as geometric shapes like circles, squares/rectangles, ellipses, parabolas, splines, etc., other non-geometric cutouts or troughs, or virtually any other concave shape that may be utilized to facilitate articulation of a femoral component relative to a tibial insert, while at the same time generally progressively becoming less constraining in the medial-to-lateral frontal cross-section to decrease the congruence between the variable articular surface and the articular surfaces of the femoral component (e.g., along the entire length of the tibial insert, or partially along the length of the tibial insert, such as partially or entirely within an anterior and/or posterior half of the tibial insert) when the femoral component moves anteriorly to posteriorly from extension to flexion.

Although several embodiments have been described in detail for purposes of illustration, various modifications may be made without departing from the scope and spirit of the invention. Accordingly, the invention is not to be limited, except as by the appended claims.

What is claimed is:

1. A tibial insert, comprising:
   a base including a coupling for attachment to a tibial baseplate; and
   an upwardly presented variable articular surface formed from the base comprising a concave geometry having a medial-to-lateral cross-sectional surface becoming progressively larger anteriorly to posteriorly at least partially along a length of a posterior portion of the tibial insert.

2. The tibial insert of claim 1, wherein the articular surface is anteriorly-to-posteriorly symmetrical.

3. The tibial insert of claim 1, wherein the articular surface is medially-to-laterally symmetrical.

4. The tibial insert of claim 1, wherein the tibial insert comprises a singular component implantable with a medial condyle component or a lateral condyle component in a left knee unicompartmental knee replacement and a right knee unicompartmental knee replacement.

5. The tibial insert of claim 1, wherein the concave geometry is relatively more lofted at an anterior edge of the tibial insert than midway between the anterior edge and a posterior edge.

6. The tibial insert of claim 1, wherein the concave geometry is relatively more lofted at a posterior edge of the tibial insert than midway between the posterior edge and an anterior edge.

7. The tibial insert of claim 1, wherein the coupling includes a trough formed within the base having a depth to receive a quantity of cement sufficient to couple the base to the tibial baseplate.

8. The tibial insert of claim 1, wherein the concave geometry comprises a circular curve or a trough.

9. The tibial insert of claim 1, wherein the articular surface is asymmetrical.

10. The tibial insert of claim 1, wherein the posterior portion of the tibial insert is between a posterior edge and midway between the posterior edge and an anterior edge.

11. A tibial insert, comprising:
a base including a coupling for attachment to a tibial baseplate; and
an articular surface formed from the base and including a pair of concave geometries tapering interiorly in height and having a progressively increasing congruence, with an articulating surface of a femoral component, in a medial-to-lateral cross-section from a respective anterior edge or a posterior edge to a center of the tibial insert.

12. The tibial insert of claim 11, wherein the tibial insert comprises a singular component implantable with a lateral condyle component or a medial condyle component in either a right knee unicompartmental knee replacement or a left knee unicompartmental knee replacement.

13. The tibial insert of claim 11, wherein each of the pair of concave geometries are symmetrical relative to one another about a coronal plane.

14. The tibial insert of claim 11, wherein the pair of concave geometries are asymmetrical relative to one another.

15. The tibial insert of claim 11, wherein at least one of the concave geometries comprises a circular curve, a parabolic curve, an elliptical curve, or a spline curve, or a trough.

16. The tibial insert of claim 11, wherein the articular surface at least partially tapers interiorly in height between at least one of the anterior edge or the posterior edge and the center between the anterior edge and the posterior edge.

17. A tibial insert, comprising:
a base including a coupling for attachment to a tibial baseplate; and
an articular surface formed from the base having a symmetrical medial-to-lateral cross-section surface becoming relatively larger at a posterior edge and an anterior edge of the base than at a center thereof independent of the orientation of the tibial insert in a left unicompartmental knee replacement or a right unicompartmental knee replacement.

18. The tibial insert of claim 17, wherein the tibial insert comprises a singular component and the articular surface is anterior-to-posterior symmetrical, wherein the tibial component is implantable with a medial condyle component or a lateral condyle component in a left knee unicompartmental knee replacement and a right knee unicompartmental knee replacement.

19. The tibial insert of claim 17, wherein the symmetrical medial-to-lateral cross-section opening comprises a troughed geometry tapering from the posterior edge and tapering from the anterior edge to the center of the tibial insert.

20. The tibial insert of claim 17, wherein the articular surface includes a variable radius of curvature relatively larger than a constant radius of curvature of a translating surface of a femoral component between a ratio of 5:1 at ninety degrees flexion and a ratio of 2.5:1 at zero degrees flexion.

21. The tibial insert of claim 20, wherein the translating surface of the femoral component maintains a relatively constant contact patch with the articular surface of the tibial insert between zero degrees flexion and ninety degrees flexion.

22. The tibial insert of claim 20, wherein the variable radius of curvature permits at least ±10 degrees of internal or external rotation of the femoral component relative to the tibial insert between zero degrees flexion and ninety degrees flexion.

23. The tibial insert of claim 17, wherein the coupling comprises a bone cement selected from the group consisting of a polymethylmethacrylate (PMMA) adhesive, a fibrin adhesive, a collagen adhesive, a polyurethane adhesive, an epoxy resin adhesive, a cyanoacrylate adhesive, a polyester adhesive, and a zinc polycarboxylate adhesive.

24. The tibial insert of claim 17, wherein the coupling comprises a cementless attachment.

* * * * *